US012329955B2

(12) United States Patent
Straube et al.

(10) Patent No.: US 12,329,955 B2
(45) Date of Patent: *Jun. 17, 2025

(54) INTRAVASCULAR MEMBRANE OXYGENATOR CATHETER WITH OSCILLATING HOLLOW FIBER MEMBRANES

(71) Applicant: Duke University, Durham, NC (US)

(72) Inventors: Tobias Straube, Durham, NC (US); Stewart Farling, Durham, NC (US); Bruce Klitzman, Durham, NC (US); Marc Deshusses, Durham, NC (US); Travis Vesel, Durham, NC (US); Ira Cheifetz, Durham, NC (US)

(73) Assignee: Duke University, Durham, NC (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/226,539

(22) Filed: Jul. 26, 2023

(65) Prior Publication Data
US 2023/0372694 A1 Nov. 23, 2023

Related U.S. Application Data

(63) Continuation of application No. 17/962,966, filed on Oct. 10, 2022, now Pat. No. 11,771,883.
(Continued)

(51) Int. Cl.
*A61M 60/122* (2021.01)
*A61M 60/13* (2021.01)

(52) U.S. Cl.
CPC ......... *A61M 60/122* (2021.01); *A61M 60/13* (2021.01)

(58) Field of Classification Search
CPC .. A61B 2018/00184; A61B 2018/0019; A61B 2018/00196; A61B 2018/00202;
(Continued)

(56) References Cited

U.S. PATENT DOCUMENTS

| 4,583,969 A | 4/1986 | Mortensen |
| 4,631,053 A | 12/1986 | Taheri |

(Continued)

FOREIGN PATENT DOCUMENTS

WO   WO-02076530 A1 * 10/2002 .......... A61M 1/1678

OTHER PUBLICATIONS

Farling et al., "Development of a novel intravascular ocygenator catheter: Oxygen mass transfer properties across nonporous hollow fiber membranes." Biotechnology and Bioengineering, 2020; 1-12.
(Continued)

*Primary Examiner* — Adam Marcetich
(74) *Attorney, Agent, or Firm* — Quarles & Brady, LLP

(57) ABSTRACT

The present disclosure describes intravascular oxygenation systems and methods with one or more of improved oxygen diffusion flux, improved resistance to bubble formation on the surface of non-porous hollow fibers, and reduced size. The systems and methods include a pneumatic inlet coupled to a pneumatic source that provides a gas containing oxygen at a high pressure. A plurality of hollow fiber membranes (HFM) are in pneumatic communication with the pneumatic inlet to receive the gas containing oxygen and with an outlet to exhaust a partially deoxygenated gas. An electronic controller drives the motor to oscillate the plurality of HFMs to cause a diffusive flux of the gas containing oxygen from the plurality of HFMs into a region of interest of a subject. The electronic controller may drive the motor according to an oscillation pattern, which may include a macro-oscillation with superimposed micro-oscillations.

20 Claims, 32 Drawing Sheets

Related U.S. Application Data

(60) Provisional application No. 63/254,208, filed on Oct. 11, 2021.

(58) Field of Classification Search
CPC ...... A61B 2018/00208; A61M 1/1678; A61M 1/26; A61M 1/262; A61M 1/265; A61M 1/1625

See application file for complete search history.

(56) References Cited

U.S. PATENT DOCUMENTS

| | | | | |
|---|---|---|---|---|
| 4,889,137 | A | * | 12/1989 | Kolobow ................ A61F 2/88 606/191 |
| 5,037,383 | A | | 8/1991 | Vaslef et al. |
| 5,098,376 | A | | 3/1992 | Berry et al. |
| 5,158,581 | A | | 10/1992 | Coplan |
| 5,336,164 | A | | 8/1994 | Snider et al. |
| 5,376,069 | A | | 12/1994 | Hattler |
| 5,776,047 | A | | 7/1998 | Fukunaga et al. |
| 5,788,668 | A | | 8/1998 | Leonhardt |
| 5,814,011 | A | * | 9/1998 | Corace ................ A61M 60/237 604/23 |
| 6,193,677 | B1 | | 2/2001 | Cady |
| 6,196,990 | B1 | | 3/2001 | Zicherman |
| 6,581,233 | B1 | | 6/2003 | Cheng |
| 7,090,792 | B1 | * | 8/2006 | Balding ................ F28F 21/062 264/339 |
| 2002/0143397 | A1 | | 10/2002 | von Segesser |
| 2003/0073946 | A1 | | 4/2003 | Gorsuch et al. |
| 2003/0163146 | A1 | | 8/2003 | Epstein et al. |
| 2005/0187508 | A1 | | 8/2005 | Gorsuch et al. |
| 2005/0215936 | A1 | | 9/2005 | Gorsuch et al. |
| 2005/0232811 | A1 | | 10/2005 | Autschbach et al. |
| 2005/0281705 | A1 | * | 12/2005 | Mortensen ............. A61M 1/16 422/45 |
| 2006/0264810 | A1 | | 11/2006 | Hattler et al. |
| 2008/0275343 | A1 | | 11/2008 | Hoffman |
| 2010/0198206 | A1 | | 8/2010 | Levin |
| 2010/0331767 | A1 | | 12/2010 | Frankowski et al. |
| 2012/0157905 | A1 | | 6/2012 | Sehgal |
| 2015/0141905 | A1 | * | 5/2015 | Spears ................ A61M 5/142 604/24 |
| 2016/0193438 | A1 | | 7/2016 | White et al. |
| 2018/0138834 | A1 | | 5/2018 | Hamamoto et al. |
| 2018/0185557 | A1 | | 7/2018 | Karimov et al. |
| 2019/0298404 | A1 | | 10/2019 | Stritch |
| 2019/0314567 | A1 | | 10/2019 | Straube et al. |
| 2022/0080106 | A1 | | 3/2022 | Evans et al. |
| 2022/0152362 | A1 | * | 5/2022 | Evans ............... A61M 25/1002 |

OTHER PUBLICATIONS

Straube et al., "Intravascular Gas Exchange: Physiology, Literature Review, and Current Efforts," Respiratory Care, 2022, vol. 67, No. 4, 480-493.

* cited by examiner

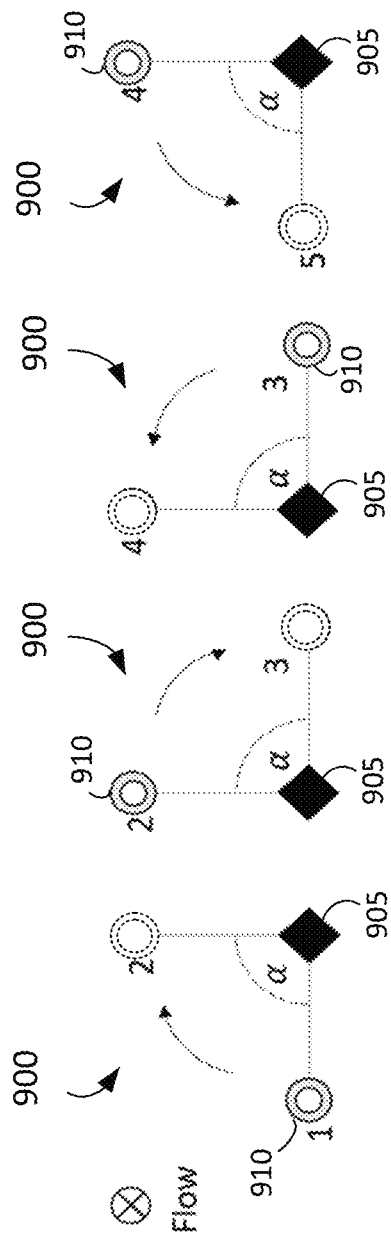
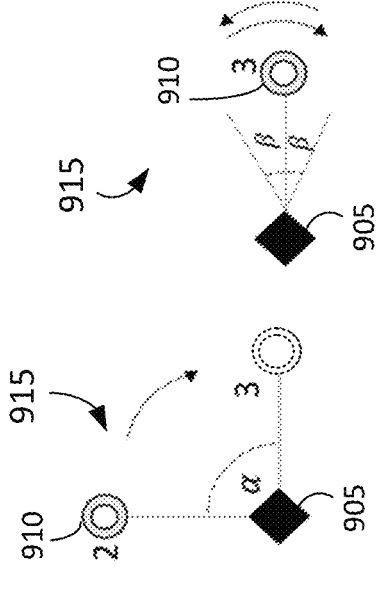
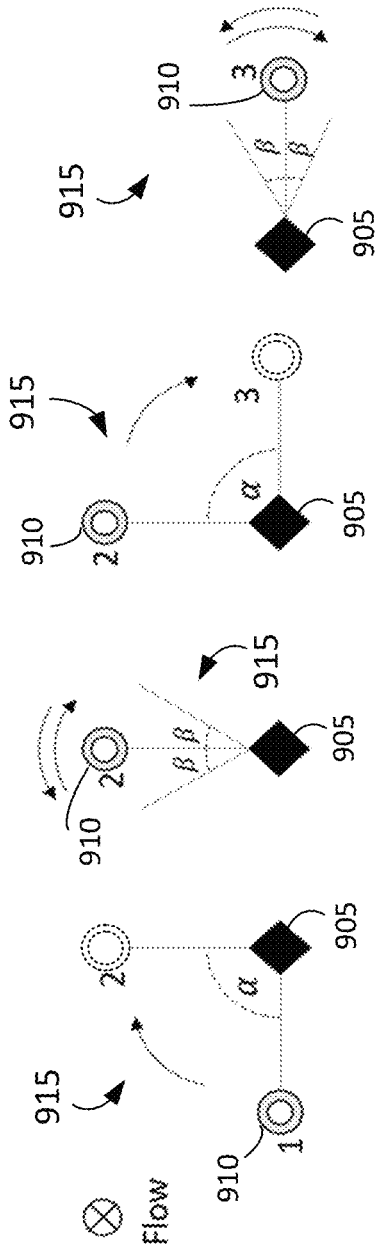

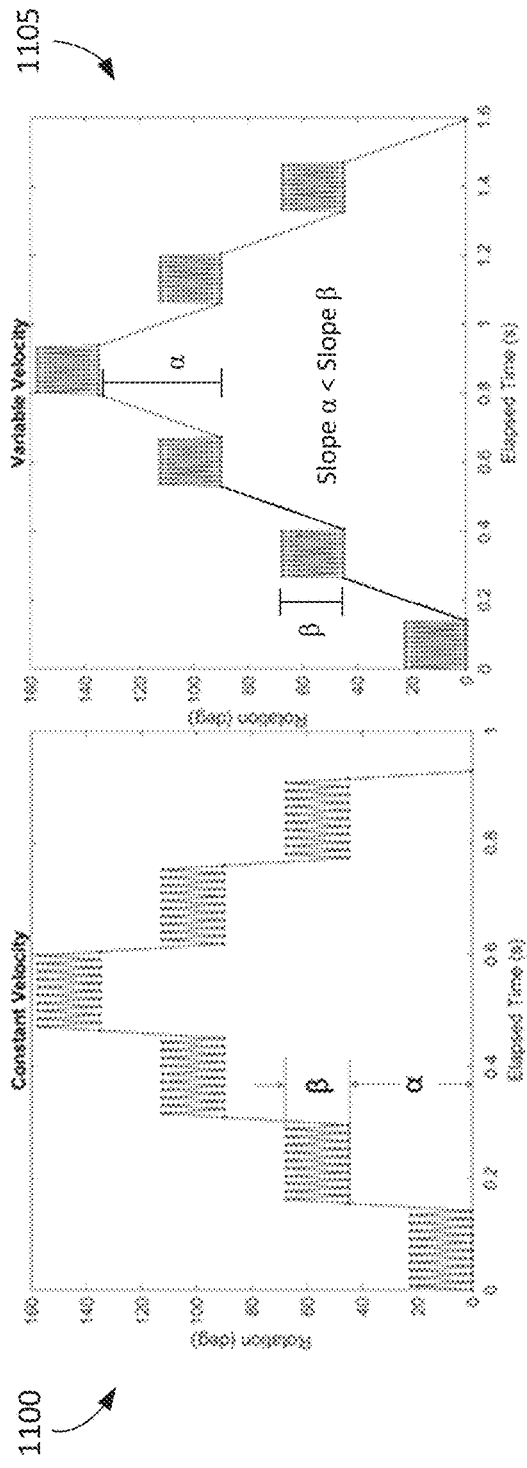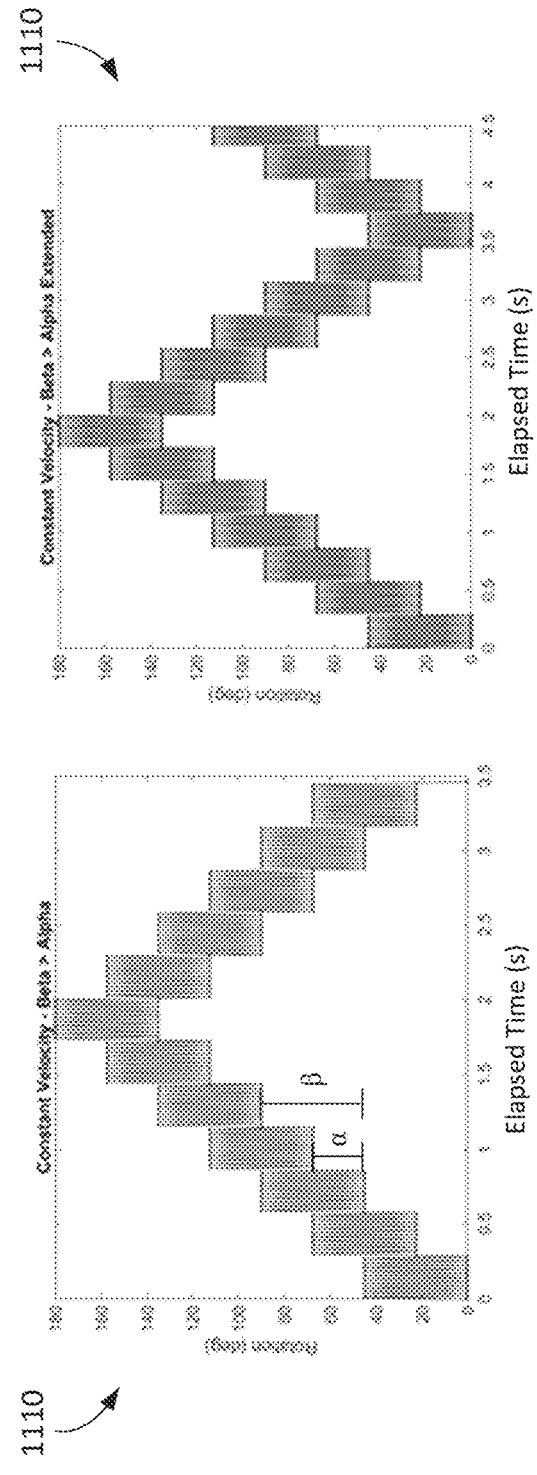
FIG. 11A
FIG. 11B
FIG. 11C
FIG. 11D

Single 'leaf'

Double 'leaf'

Triple 'leaf'

Half wrap expanded

Triple wrap expanded

Triple wrap compressed

Half wrap
Double leaf
Expanded

Double wrap
Double leaf
Expanded

Double wrap
Double leaf
Contracted

INTRAVASCULAR MEMBRANE OXYGENATOR CATHETER WITH OSCILLATING HOLLOW FIBER MEMBRANES

RELATED APPLICATIONS

The present application is a continuation application of U.S. patent application Ser. No. 17/962,966, filed Oct. 10, 2022, which is based on and claims priority from U.S. Patent Application No. 63/254,208, filed on Oct. 11, 2021, the entire disclosure of each of which is incorporated herein by reference.

FEDERAL FUNDING LEGEND

This invention was made with government support under Federal Grant no. 1T32HD094671-01A1 awarded by the National Institute of Child Health and Human Development (NIH/NICHHD). The government has certain rights to this invention.

BACKGROUND

Acute respiratory failure with inadequate oxygenation and/or ventilation is a common reason for intensive care unit (ICU) admission in children and adults. When mechanical ventilation fails to adequately oxygenate a patient, other oxygenation systems may be used. One potential option is veno-venous extracorporeal membrane oxygenation (VV-ECMO). ECMO directly oxygenates blood independent of the lungs and, therefore, is capable of fully supporting a patient regardless of degree of lung injury.

SUMMARY

Veno-venous extracorporeal membrane oxygenation (VV-ECMO or ECMO) used for directly oxygenating blood is associated with potential complications, including hemorrhage, thrombosis, and, infection. Further, ECMO is only available in approximately 9% of hospitals in the United States and fewer worldwide. The complexity and expense of ECMO, its associated morbidity, and its low availability limit the benefits of this potentially life-saving technology. There is a need for alternative technologies that support patients with severe respiratory failure that function independently of diseased lungs. In this light, novel therapies such as an intravascular gas exchange device are an attractive option. Previous systems developed for intravascular oxygenation have been unsuccessful due to, among other reasons, their reliance on a large surface area to generate significant gas exchange which resulted in bulky catheters too large for intravascular use.

Systems and methods described herein are able to provide intravascular oxygenation for patients and overcome challenges presented by EMCO and other intravascular oxygenation systems using a combination of (i) high-pressure oxygenated gas (e.g., at or above 1.1 bar absolute pressure, between 1.1 bar and 2.0 bar of absolute pressure, or between 1.1 bar 5.0 bar absolute pressure) to generate a large driving gradient across a non-porous diffusing surface of hollow fiber membranes and (ii) angular or rotational oscillations of the HFMs to further enhance the oxygen transfer efficiency. Additionally, the rotational oscillations may include micro-oscillations superimposed on macro-oscillations. By combining the high-pressure oxygen gradient across non-porous HFMs undergoing angular oscillation, particularly with superimposed micro-oscillations, the impacts of both internal and external barriers to oxygen mass transfer are reduced and high oxygen transfer efficiencies are achieved for clinically significant intravascular oxygen delivery.

Oxygenation systems and methods provided herein use hyperbaric intraluminal oxygen pressure, which enables high diffusion through HFMs, combined with oscillations of the HFMs that increase the efficiency of the diffusion through the HFMs relative to static HFMs. In some examples, micro-oscillations are superimposed on the oscillations (i.e., on oscillations of larger angles, also referred to as macro-oscillations), which can ensure that oxygen in the HFMs that is diffused through the HFMs is dissolved into solution (into a subject's blood) with decreased or no bubble formation. Because these oscillation techniques decrease or eliminate bubbles, the HFMs can operate at hyperbaric pressure and at higher levels than previously employable. Further, because higher pressure levels can be used, an increase in oxygen flux and transfer efficiency results. Further, the increased oxygen flux and transfer efficiency (using hyperbaric pressure and oscillation) enables reduction in gas diffusing surface area of the HFMs. In other words, the size of the HFM bundle may be more compact and, thus more amenable to intravascular use.

Some embodiments of the disclosure provide an oxygenation system. The oxygenation system can include a pneumatic inlet, a plurality of hollow fiber membranes (HFMs), a motor, and an electronic controller. The pneumatic inlet can be configured to couple to a pneumatic source that provides a gas containing oxygen at a pressure at or above 1.1 bar of absolute pressure. The plurality of HFMs can be in pneumatic communication with the pneumatic inlet to receive the gas containing oxygen. The motor can be coupled to the plurality of HFMs. The electronic controller can be coupled to the motor and can be configured to drive the motor to oscillate the plurality of HFMs to cause a diffusive flux of the gas containing oxygen from an interior of the plurality of HFMs in a region of interest of a subject.

Some embodiments of the disclosure provide a method for intravascular oxygenation. The method can include receiving, by a pneumatic inlet coupled to a pneumatic source, a gas containing oxygen at a pressure at or above 1.1 bar of absolute pressure, receiving, by a plurality of hollow fiber membranes (HFMs) in pneumatic communication with the pneumatic inlet, the gas containing oxygen, and driving, by an electronic controller, a motor to oscillate the plurality of HFMs to cause a diffusive flux of the gas containing oxygen from an interior of the plurality of HFMs in a region of interest of a subject.

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

BRIEF DESCRIPTION OF THE DRAWINGS

The accompanying drawings, which are incorporated in and form a part of this specification, illustrate embodiments of the disclosure and, together with the description, explain principles of the embodiments.

FIGS. 9A-9D illustrate an oscillation pattern according to some embodiments.

FIGS. 9E-9H illustrate another oscillation pattern according to some embodiments.

FIGS. 11A-11F and 11H-11K illustrate further examples of rotational oscillation patterns in the form of plots of rotation angle versus time.

DETAILED DESCRIPTION

Figure 1A:
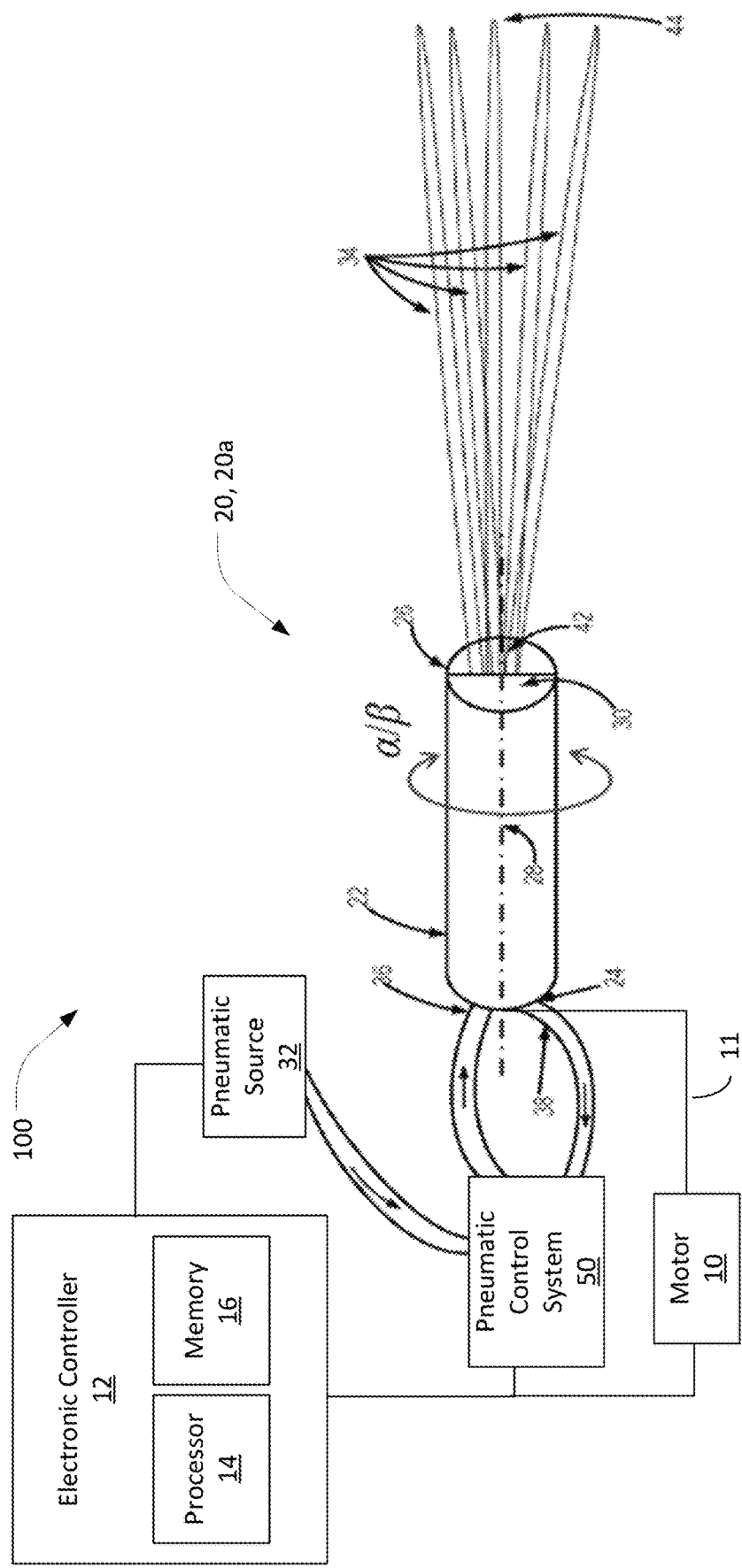
FIG. 1A is a schematic diagram of an intravascular oxygenation system according to some embodiments of this invention.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

Furthermore, the disclosed subject matter may be implemented as a system, method, apparatus, or article of manufacture using standard programming and/or engineering techniques and/or programming to produce hardware, firmware, software, or any combination thereof to control an electronic based device to implement aspects detailed herein.

Unless specified or limited otherwise, the terms "connected," and "coupled" and variations thereof are used broadly and encompass both direct and indirect mountings, connections, supports, and couplings. Further, "connected" and "coupled" are not restricted to physical or mechanical connections or couplings. As used herein, unless expressly stated otherwise, "connected" means that one element/feature is directly or indirectly connected to another element/feature, and not necessarily electrically or mechanically. Likewise, unless expressly stated otherwise, "coupled" means that one element/feature is directly or indirectly coupled to another element/feature, and not necessarily electrically or mechanically.

As used herein, the term "processor" may include one or more processors and memories and/or one or more programmable hardware elements. As used herein, the term "processor" is intended to include any of types of processors, CPUs, microcontrollers, digital signal processors, or other devices capable of executing software instructions.

As used herein, the term "memory" includes a non-volatile medium, e.g., a magnetic media or hard disk, optical storage, or flash memory; a volatile medium, such as system memory, e.g., random access memory (RAM) such as DRAM, SRAM, EDO RAM, RAMBUS RAM, DR DRAM, etc.; or an installation medium, such as software media, e.g., a CD-ROM, or floppy disks, on which programs may be stored and/or data communications may be buffered. The term "memory" may also include other types of memory or combinations thereof.

The term "flux" or "diffusive flux" refers to Fick's diffusion laws that a flux goes from regions of high concentration to regions of low concentration, with a magnitude that is proportional to the concentration gradient (spatial derivative). In simplistic terms, diffusive flux refers to the concept that a solute will move from a region of high concentration to a region of low concentration across a concentration gradient. The flux or diffusive flux can be measured as a transmission rate from the region of high concentration to the region of low concentration, in some aspects in milliliters (mL) per minute. In a non-limiting aspect, the flux or diffusive flux can be measured as a transmission rate from the inside of a device as described herein into a volume of water or a volume of blood. Flux or diffusive flux can be quantified by measuring dissolved oxygen. In fact, dissolved oxygen by definition only includes flux that is dissolved in solution and is not a bubble. However, using a dissolved oxygen (DO) probe does not indicate if there are or aren't bubbles, it just indicates the amount of oxygen that is dissolved.

The term "nonporous" refers to a solid wall that does not allow direct communication from an interior side of the nonporous wall across or through it to an exterior side of the wall, allowing molecular transport only via diffusion rather than convection. Nonporous means there are no pores, even at the nano, pico, or atto scale, and the solid wall is continuous such that the material of the solid wall has no discontinuities. The term "porous" refers to a wall having pores that allow convection from an interior side of the porous wall through the pores to an exterior side of the wall. The pores in the porous wall have a diameter at or above approximately 0.1 microns to 1 micron, the pores in the porous wall can also have a diameter of 0.05 microns to 0.1 micron or smaller. A pore could also be defined as a discontinuity in the material comprising the wall, and the term porous can encompass terms such as "microporous" since this term refers to a porous or a material having discontinuity.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human who is undergoing a blood oxygenation procedure using the systems and methods described herein.

Unless otherwise defined, all technical terms used herein have the same meaning as commonly understood by one of ordinary skill in the art to which this disclosure belongs.

The present disclosure builds upon the membrane oxygenation described in U.S. patent application Ser. No. 15/950,517 (Intravascular Membrane Oxygenator Catheter Systems and Methods), incorporated herein by reference. The previously disclosed solution utilizes high pressure oxygen provided through small non-porous hollow fiber membranes (HFMs) to generate a large transmural gradient for diffusion, which results in a high mass transfer efficiency. However, under certain operating conditions that generate a high oxygen flux, small oxygen bubbles have been noted to form on the abluminal surface of the HFMs. Generally, bubbles (or gaseous emboli) are not desired in a bloodstream because bubbles can block small capillaries throughout the body, thereby decreasing blood flow (for example, in the pulmonary capillaries limiting blood flow to the lungs), and because bubbles may induce inflammation and activate clotting within the bloodstream. The present disclosure addresses these and other challenges by providing systems and methods to further enhance oxygen mass transfer efficiency while limiting the formation of bubbles on the abluminal surface of the HFMs.

For example, one aspect of the present disclosure provides an intravascular oxygenation system and method with improved oxygen diffusion flux and bubble reduction through oscillation of HFMs of the system. More particularly, in some examples, an intravascular oxygenation system is provided with a pneumatic inlet and outlet, a plurality of hollow fiber membranes (HFMs), a motor, and an electronic controller. The electronic controller can be coupled to the motor and configured to drive the motor to oscillate the plurality of HFMs to cause (or increase) a diffusive flux of a gas containing oxygen received at the pneumatic inlet from the plurality of HFMs into a region of interest of a subject. In some examples, the oscillation of the HFMs includes rotational oscillation with micro-oscillations superimposed on macro-oscillations, which can further reduce bubble generation in an oxygenation system. Generally, as pressure of the oxygenated gas in the HFMs 34 increases, diffusive flux of oxygen increases and bubble formation increases. However, oscillating the HFMs, particularly rotationally oscillating the HFMs with micro-oscillations superimposed on macro-oscillations, reduces the bubble formation, thereby enabling an increase in the pressure of the oxygenated gas and in the resulting diffusive flux of oxygen into blood without the corresponding increase in bubbles.

The improved resistance to bubble formation (and improved oxygen flux) can be attributed to one or more underlying mechanisms related to the oscillation of the HFMs. For example, oscillation causing the movement of HFMs in a direction perpendicular to blood flow can create a higher effective shear flow that reduces the opportunity for bubble formation. The oscillations have been shown to disturb blood boundary layer formation around each individual HFM allowing more oxygen to be dissolved. Moreover, even if microbubbles form on the surface of the HFM, the microbubble are disrupted by the oscillatory movement of the HFMs and swept away into the bloodstream to be dissolved prior to coalescing into larger clinically significant bubbles. Additionally, oscillating the HFMs using superimposed angular oscillations can increase convective mixing by disrupting secondary flow patterns of the blood and increase the relative velocity of blood flowing past the HFM, which can reduce liquid boundary layer formation. These mechanisms both serve to reduce bubble formation and increase oxygen flux. Also, superimposed angular oscillations can induce movement such that the HFMs may have less opportunity for fiber-to-fiber contact in the vascular path, which could otherwise reduce efficiency. Further, the oscillations may induce vibrations along the fiber, and/or the motion of the oscillator can also directly or indirectly create a longitudinal wave along the length of the HFM, either or both of which may dislodge microscopic bubbles before they grow in size, increase convective mixing, and reduce liquid boundary layer formation.

FIG. 1A shows an intravascular oxygenation system 100 according to an aspect of the disclosure. The oxygenation system 100 can include a catheter 20a (also referred to as catheter 20) that further includes a catheter shaft 22 extending from a proximal end 24 to a distal end 26 along a longitudinal axis 28 to define a lumen 30. The catheter 20a is connected to a pneumatic source 32 in pneumatic communication with the catheter 20a at the proximal end 24. The pneumatic source 32 may be a high-pressure source of gas containing oxygen that may be pressure, flow, and temperature regulated to supply regulated gas containing oxygen to the catheter 20a. In some non-limiting aspects, the pneumatic source 32 can be a pneumatic tank, such as a medical grade oxygen tank. In other non-limiting aspects, the pneumatic source 32 can be a pneumatic pump. The pneumatic source 32 is in pneumatic communication with a pneumatic control system 50. The pneumatic control system 50 may include one or more valves to control the flow of gas from the pneumatic source 32 to and the catheter 20a and from the catheter 20a to an ambient environment of the system 50.

The lumen 30 of the catheter shaft 22 is configured to receive a plurality of hollow fiber membrane loops (HFMs) 34 of the catheter 20a that are in pneumatic communication with the pneumatic source 32 via the pneumatic control system 50 via a pneumatic inlet 36 configured to provide high pressure gas containing oxygen to the HFMs 34. The HFMs 34 may be supported by a manifold 42 of the catheter shaft 22 that extends into the lumen 30 and provides a plurality of openings to receive the HFMs 34 such that the HFMs 34 may be retained or thermoset in the manifold 42 of the lumen 30. The HFMs 34 may also be retained or thermoset in a manifold at the proximal end 24 of the catheter shaft 22 and then travel within catheter shaft 22 exiting at the distal end 26 through manifold 42. In some non-limiting aspects, the HFMs 34 can be retained in the manifold 42 using a high strength epoxy or other suitable materials for securely potting the HFMs 34 in the manifold 42. In some examples, spacers (e.g., wire spacers) are included in the catheter 20a and/or the bundle of HFMs 34 to space out HFMs 34, or the HFMs 34 may have intrinsic memory so that when the HFMs 34 are deployed within a vasculature of a subject, the HFMs 34 can spread out into a spaced configuration. Such spacers may also be provided in other embodiments of the catheter 20 described below.

In some embodiments of the present disclosure, the HFMs 34 can be looped such that an inlet side is connected to the pneumatic source 32 via the pneumatic inlet 36 and the inlet side can extend to the distal end 26 of the catheter 20a where the inlet side transitions to the return side of the HFMs 34. The return side of the HFMs 34 can pneumatically communicate with an outlet 38 that can communicate pneumatic exhaust out of the proximal end 24 of the catheter 20a. The HFMs 34 can be arranged in parallel loops with both ends retained in the manifold 42. In other embodiments, such as described below, the individual HFMs of the bundle of HFMs 34 are not provided in a looped configuration such that an inlet and outlet side of each HFM are on opposite ends (distal and proximal ends) of the HFM bundle 34.

The oxygenation system 100 further includes an electronic controller 12. The electronic controller 12 is coupled to one or more of the pneumatic control system 50, a motor 10, and the pneumatic source 32. The electronic controller 12 includes an electronic processor 14 and a memory 16.

The electronic processor 14 and the memory 16 can communicate over one or more control buses, data buses, etc. The electronic processor 14 can be configured to communicate with the memory 16 to store data and retrieve stored data. The electronic processor 14 can be configured to receive instructions and data from the memory 16 and execute, among other things, the instructions. In particular, the electronic processor 14 executes instructions stored in and retrieved from the memory 16. The memory 16 can include read-only memory (ROM), random access memory (RAM), other non-transitory computer-readable media, or a combination thereof. The memory 16 can include instructions (e.g., software) executable by the electronic processor 14 to enable the electronic controller 12 to, among other things, control one or more of the pneumatic source 32, the pneumatic control system 50, and/or the motor 10.

For example, the controller 12 may execute software (e.g., the electronic processor 14 may execute software stored on the memory 16) to regulate the pressure, flow, and temperature of the gas from the pneumatic source 32. This regulation may include receiving sensor data from corresponding sensors that indicate one or more of the pressure, flow, and temperature of the gas, and controlling pressure, flow, and temperature regulating devices (pumps, valves, solenoids, heaters, cooling elements, etc.) based on the sensor data to provide the gas at a desired pressure, flow, and temperature.

Further, the controller 12 may execute software to control the pneumatic control system 50. For example, the pneumatic control system 50 may include at least one controllable inlet valve to control the pressure and/or flow of gas from the pneumatic source 32 to the inlet 36 and at least one controllable exhaust valve to control the pressure and/or flow of gas from the outlet 38 of the catheter 20a to an ambient environment of the system 50 (or other exhaust repository). The controller 12 may determine characteristics of the system 100 (e.g., based on sensor data from one or more sensors). For example, the pneumatic control system 50 can have a plurality of gas flow meters and pressure gauges that can be calibrated to accurately measure and indicate to the controller 12 a flow rate and pressure of gas being delivered to the catheter 20a (e.g., at the inlet 236). Similarly, the pneumatic control system 50 can have a plurality of gas flow meters and pressure gauges that can be calibrated to accurately measure and indicate to the controller a flow rate and pressure of the exhausted gas from the catheter 20a (e.g., at the outlet 238).

In response to the sensor data provided by the one or more gas flow meters and pressure gauges, the controller 12 may control the inlet and exhaust vales to control the flow of gas in and out of the catheter 20a. For example, the control signals may be analog voltage signals (e.g., between 0 and 5 volts), where the voltage indicates the degree to which a particular valve should be opened (e.g., 2 volts=40% open, 4 volts=80% open, etc.). In some examples, the controller 12 may maintain a desired flow rate and/or pressure for the gas within the bundle of HFMs 34 by controlling the inlet and exhaust valve(s), where, generally, increasing the degree to which the inlet valve(s) are open will increase the pressure and increase the flow rate; decreasing the degree to which the inlet valve(s) are open will decrease the pressure and decrease the flow rate; increasing the degree to which the exhaust valve(s) are open will decrease the pressure and increase the flow rate; decreasing the degree to which the exhaust valve(s) are open the exhaust valve(s) will increase the pressure and decrease the flow rate. This combination of inlet and outlet valve control allows the system to operate at similar average pressures within the HFMs 34 at varying gas flow rates through the fiber. This ability to control both the average pressure and the flow rate can enable the system to maintain a minimum amount of oxygen flowing through the HFMs 34 to constantly deliver fresh oxygen through the fiber without significant back diffusion impacts of water vapor into the HFMs 34.

Thus, the controller 12 and the pneumatic control system 50 can control the pressure and flow rate of gas containing oxygen provided to the catheter 20a allowing precise titration with continuous monitoring to match a patient's needs. In some examples, the controller 12, based on clinician input (e.g., via a user interface in communication with the controller 12) can control the pneumatic control system 50 to titrate oxygen pressure and flow through the HFMs 34 in the catheter 20a to change oxygen transmission rate as needed by the patient. Thus, the controller 12 and the pneumatic control system 50 can be capable of controlling the pressure and flux of oxygen based on the inputs supplied by a clinician.

Further, the controller 12 may execute software to control the motor 10. In some examples, the motor 10 is a steppermotor. In other examples, the motor 10 is another type of motor, such as a permanent magnet brushless DC motor. The motor 10 is coupled to the bundle of HFMs 34 such that rotation of the motor 10 causes rotation of the bundle of HFMs 34. For example, a rotor of the motor 10 may be coupled to a drive shaft 11 that is ultimately coupled to the bundle of HFMs 34. For example, the drive shaft 11 may be a thin, flexible shaft that extends through the vasculature of the patient with the catheter 20a. A distal end of the drive shaft 11 may be coupled to the manifold 42 that is retaining the bundle of HFMs 34. Accordingly, driving the motor 10 to rotate or oscillate, causes the bundle of HFMs 34 to rotate or oscillate. Alternatively, the motor 10 can be magnetically coupled to the bundle of HFMs 34 via extracorporeal magnets to cause rotation or oscillation of the bundle HFMs 34.

As described in further detail below, the controller 12 may control the motor 10 to oscillate (and, thus, the bundle of HFMs 34 to oscillate) according to various oscillation patterns. For example, to implement some oscillation patterns, the electronic controller 12 drives the motor 10 to provide superimposed angular oscillations to the HFMs 34. As also described further below, the oscillation of the bundle of HFMS 34 causes a diffusive flux of the gas containing oxygen from the bunded HFMs 34 into a region of interest of a subject. In particular, the oscillation increases the diffusive flux of the gas relative to a static (non-rotating) bundle of HFMs and relative to a constantly or unidirectionally rotating bundle of HFMs.

Although the electronic controller 12 is illustrated as a single device in FIG. 1A (and in FIG. 2A, described below), the electronic controller 12 may include one or more controllers each with a respective processor, memory, and/or circuitry to implement the functionality of the controller 12 described herein. For example, the electronic controller 12 may include a motor controller coupled to the motor 10 and performing the motor control functions described herein (e.g., driving the motor 10 to oscillate the HFMs 34) and a pneumatic controller coupled to the pneumatic control system 50 and performing the pneumatic control functions described herein (e.g., opening and closing valves, controlling flow rate, de-pressurizing the HFMs 34, etc.).

Figure 1B:
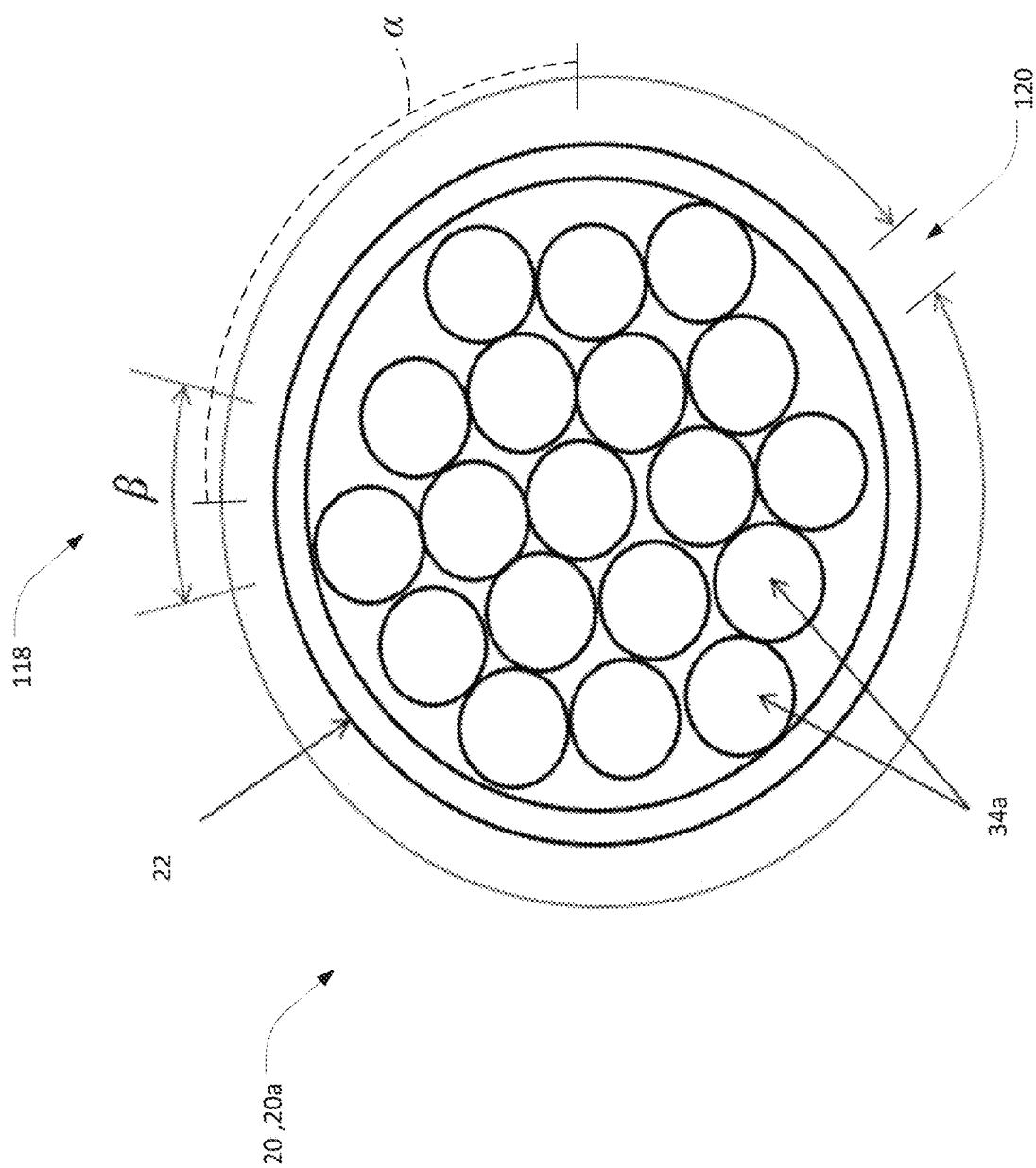
FIG. 1B is a cross-sectional view of a catheter lumen containing hollow fiber membranes (HFMs) of the oxygenation system of FIG. 1.

FIG. 1B shows a cross-sectional view of the bundle of HFMs 34 shown in FIG. 1A. The bundle of HFMs 34 is illustrated within catheter shaft 22. The bundle of HFMs 34 is illustrated as included eighteen HFMs, two of which are labeled HFMs 34a. However, the particular number of HFMs within the bundle of HFMs 34 may vary. FIG. 1B also illustrates examples of oscillations resulting from driving of the motor 10, including macro-oscillations 120 and micro-oscillations 118. In the example embodiment of FIG. 1B, the macro-oscillations 120 are in the range of approximately 360°, with α representing an example step of the macro-oscillations 120 of approximately 90°, and β represents the micro-oscillations in the range of approximately 15°. However, the macro-oscillations 120 for the system 100 may be in the range of approximately 1-360° (or a narrower range, such as 22.5-360°, 22.5-180°, 45-180°, or 90-180°, etc.), with steps α of the macro-oscillation 120 being in a range of 1-360° (or a narrower range, such as 22.5-360°, 22.5-180°, 45-180°, or 90-180°, etc.), and the micro-oscillations may be in the range of approximately 1-180° (or a narrower range, such as 5-45°, 15-30°, 22.5-45°, or 30-90°, etc.). In some examples, macro-oscillations or micro-oscillations of the bundle of HFMs 34, but not both, are provided in the system 100. Further description of various techniques for oscillating the bundle of HFMs 34 is provided below.

Figure 2A:
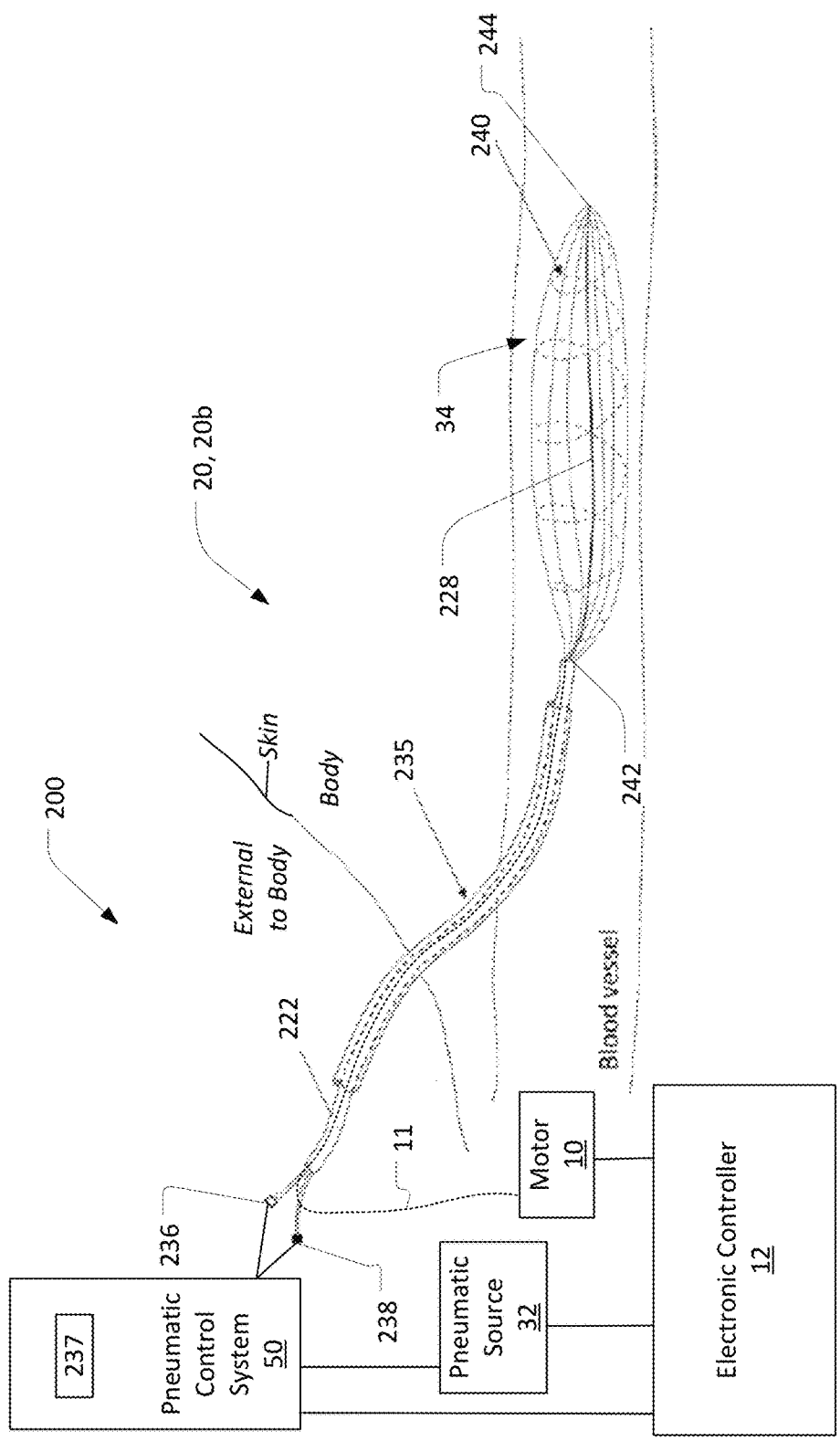
FIG. 2A is a schematic diagram of another intravascular oxygenation system according to some embodiments of this invention.

Referring now to FIG. 2A, an intravascular oxygenation system 200 is provided. The system 200 is similar to the system 100, except for the differences noted herein, and like parts are described and identified with like names and labels. In the system 200, the bundle of HFMs 34 is provided in a non-loop arrangement and include a central shaft 228. For example, proximal ends of the HFMs 34 and the central shaft 228 may be retained in a proximal end tip 242 of a catheter 20b, and distal ends of the HFMs 34 and the central shaft 228 may be retained in a distal end tip 244 of the catheter 20b.

The pneumatic control system 50 is in pneumatic communication with the pneumatic source 32, a pneumatic inlet 236, and pneumatic outlet 238 of the catheter 20b. The catheter 20b of FIG. 2A and the catheter 20a of FIG. 1A-1B, as well as catheters 20c, 20d, 20e, 20f, and 20g described below, may generically be referred to as the catheter 20. Accordingly, references to and description of the catheter 20 may apply to each of the catheters 20a-20g unless otherwise noted. As described with respect to the system 100 of FIG. 1a, the pneumatic control system 50 can provide regulated gas (e.g., containing oxygen) to the inlet 236. The inlet 236, in turn, may be pneumatically coupled to the proximal end of the central shaft 228 at the proximal end tip 242. The central shaft 228 can extend between the proximal end tip 242 and distal end tip 244. The proximal end tip 242 can retain a proximal end of the central shaft 228 and the distal end tip 244 can retain a distal end of central shaft 228 using methods similar to those described for retaining the HFMs 34 above. For example, in some examples, the proximal ends and distal ends of HFMs 34 and central shaft 228 can be retained in the proximal end tip 242 and distal end tip 244, respectively, using a high strength epoxy or other suitable materials for securely potting the proximal and distal ends in the proximal end tip 242 and distal end tip 244, respectively.

The central shaft 228 receives gas from the pneumatic inlet 236, which travels through the central shaft 228 from the proximal end tip 242 to the distal end tip 244. The distal end tip 244 can include a pneumatic connection (or flow path) for the gas that connects the distal end of the central shaft 228 to the inlets of the HFMs 34. Accordingly, the central shaft 228 can provide the gas, received via inlet 236, to inlets of the HFMs 34 at the distal end tip 244. The outlets of the HFMs 34 are in pneumatic communication with the pneumatic outlet 238. For example, the proximal end tip 242 can include a pneumatic connection (or flow path) for gas that connects the proximal end of the HFMs 34 to the pneumatic outlet 238. Accordingly, the HFMs 34 can provide gas, received from the central shaft 228 at the distal end tip 244, to the pneumatic outlet 238 at the proximal end tip 242. Thus, in these examples, the central shaft 228 provides a forward path for the gas from the proximal end tip 242 to the distal end tip 244, and the HFMs 34 define a return path for a gas from the distal end tip 244 to the proximal end tip 242.

In some embodiments of the system 200, the inlet 236 is coupled to the proximal ends of the HFMs 34 at the proximal end tip 242 and outlet 238 is coupled to the proximal end of the central shaft 228 at the proximal end tip 242, thereby causing the flow path of the gas to be reversed. More particularly, the gas from the pneumatic control system 50 may be provided to the inlet 236, may flow into the HFMs 34 at the proximal end tip 242, may flow out of the HFMs 34 at the distal end tip 244 and enter into the distal end of the central shaft 228, may flow through the central shaft 228 and into the outlet 238 at the proximal end tip 242.

In the context of the oxygenation systems described herein, the gas transiting the inlets 36 or 236 and entering into the HFMs 34 may be referred to as oxygenated gas, and the gas exiting the HFMs 34 and transiting the outlets 38 or 238 may be referred to as deoxygenated gas. The deoxygenated gas may still have oxygen present, but because of the diffusion occurring via the HFMs 34, the deoxygenated gas exiting the HFMs 34 will have a lower level of oxygen than the oxygenated gas entering the HFMs 34.

The bundle of HFMs 34 can have a looped configuration (see FIG. 1A) or a non-looped configuration (see FIG. 2A), and HFMs 34 can further be provided in a number of arrangements including a bulb shape, a twist, a helix, a braid pattern, and others. For example, FIG. 1A shows a schematic illustration of the HFMs 34 in a looped configuration with a fanned arrangement in which the HFMs 34 spread out past the distal end 26 of the catheter shaft 22 and extend to a distal end 44 of the HFMs 34. In contrast, FIG. 2A shows a schematic illustration of the HFMs in a non-looped configuration extending between the proximal end tip 242 and the distal end tip 244 in a bulging arrangement. In some examples, the systems 100 and 200 may employ a bundle of HFMs 34 having a different configuration and/or arrangement than shown in FIGS. 1A and 2A, such as those described herein. The HFMs 34 may be configured to optimize non-laminar blood flow exposure to the HFMs 34 in terms of length, inner and outer diameter of HFMs 34, number of HFMs 34, outer diameter of the HFMs 34 bundle, and positioning of HFMs 34.

The pressure under which the gas containing oxygen flows is well under the bursting pressure of the HFMs 34 to ensure safety, and the gas flowing through the HFMs 34 is temperature and flow controlled as described above. In some examples, the pneumatic control system 50 includes safety shut-off valves that detect a drop in pressure and will instantly stop gas flow through the central shaft 228 or HFMs 34 if a leak were to develop, thereby preventing venous gas emboli formation. In some examples, the pneumatic control system can have three (3) channels that provide high pressure oxygen to the central shaft 228 or HFMs 34. The HFMs 34 can be separately grouped or "banked" into three (3) groups that can be individually monitored for pressure through each group via the three (3) channels. If there is a sudden drop in pressure, as there would be in a catastrophic failure of one or more of the HFMs 34 or the central shaft 228, the pneumatic control system 50 will sense the failure and instantly shut off gas flow through that channel (and therefore bank of HFMs 34) to prevent gas emboli (blowing gas directly into blood stream from failed hollow fiber). It is to be appreciated that the number of groups and channels described above are exemplary and any appropriate number of groups and channels can be utilized.

In some examples, the pneumatic control system 50 further includes a vacuum system 237 (see FIG. 2A) to selectively de-pressurize the HFMs 34, e.g., in the case of a detected fault or sudden drop in pressure in the HFMs 34. For example, the vacuum system 237 may include a pump that is pneumatically connected to the HFMs 34 (e.g., via the inlet 236) selectively (e.g., via a controllable valve). In the case of the electronic controller 12 detecting a fault or sudden drop in pressure, the electronic controller 12 may selectively control the controllable valve to connect the pump of the vacuum system 237 to the HFMs 34, control inlet valve(s) connected to the pneumatic source 32 and outlet valves connected to the outlet 38 to close, and enable the pump to de-pressurize the HFMs 34. The vacuum system 237 may also be present in the pneumatic control system 50 of the system 100 of FIG. 1A. To detect a sudden drop in pressure, in some examples, the electronic controller 12 may receive sensor data (e.g., from a pressure sensor of the pneumatic control system 50) indicative of the pressure of the HFMs 34 and/or the rate of change of pressure of the HFMs 34. The electronic controller 12 may compare the indicated rate of change of pressure to a sudden drop rate threshold and a total change in pressure for the associated time period (determined from the pressure data) to a sudden drop change threshold. The electronic controller 12 may, in response to determining that these thresholds are exceeded, determine that a sudden drop in pressure has occurred and de-pressurize the HFMs 34. Accordingly, the electronic controller is configured to control the vacuum system to de-pressurize the HFMs 34 in response to determining a loss of pressure in the HFMs exceeding a threshold (e.g., the sudden drop change threshold and/or the sudden drop rate threshold).

Hollow Fiber Membranes (HFMs)

The HFMs 34 of the various systems provided herein, including systems 100 and 200, receive high pressure gas containing oxygen from pneumatic control system 50. The gas containing oxygen flows through the HFMs 34 to provide diffusive flux of oxygen through the walls of the HFMs 34. In embodiments provided herein, the diffusive flux of the gas containing oxygen can have an operating range at or above 500 mL per minute per square meter.

The HFMs 34 may have small radii and, accordingly, can withstand high internal pressures according to LaPlace's Law since:

$$\text{Wall Tension} = (P)(R)$$

where P is pressure and R is the radius. The ability to safely withstand high pressure means that significant flux can be achieved with only a modest surface area.

The HFMs 34 are solid wall nonporous membranes configured to deliver oxygen using exclusively diffusion rather than convection through a porous surface. Diffusion through a porous surface risks formation of high volume and large diameter bubbles, which can be undesirable for a patient, especially at hyperbaric pressures. The high-pressure gas containing oxygen, which in some aspects may be hyperbaric, flowing through the HFMs 34 creates a driving gradient, based on Fick's laws of diffusion. The driving gradient diffuses oxygen out of an interior chamber of the HFMs 34 as it dissolves through the nonporous membrane of the HFMs 34 to an exterior side of the nonporous membrane and into, for example, blood flowing past the HFMs 34 in the region of interest of the subject. Generally, with a bundle of the plurality of HFMs 34, fluid flowing past can flow between the individual HFMs 34 to expose an increased surface area of HFMs 34 to fluid flowing past. In some aspects, a high partial pressure of oxygen generates the pressure gradient that greatly increases oxygen transmission from the HFMs 34 to a region of interest of the subject. The pressure gradient generated by the hyperbaric oxygen concentration in the HFMs 34 allows for a reduction in size of the catheter shaft 22 since it is not relying on an extraordinarily large surface area to generate diffusivity. As discussed in detail below, the hyperbaric nature of the catheter 20 provides improved intravascular oxygenation via the pressure gradient between the HFMs 34 and a region of interest. The catheter 20 can be adjusted as needed for the subject's size and can be sized to be used in a range of subjects, including, but not limited to neonatal, pediatric, and adult patients.

Catheter Sizing and Insertion

In the systems described herein, including the systems 100 and 200, the catheter 20 may include a portion of inlet and outlet tubing (e.g., inlet 36, 236 and outlet 38, 238), one or more sheathing elements, a bundle of HFMs 34, and one or more associated bundle elements (e.g., a guard (described below), a central axis (e.g., central shaft 228), an HFM support (described below), a pump (described below), and/or other aspects of the systems inserted into a subject). The catheter 20 that provides intravascular oxygenation to the subject has a reduced size due to the reliance on a large oxygen concentration gradient driving diffusion rather than convection through a porous wall. The reduced size of the catheter 20 dimensioned for insertion into a region of interest, improves biocompatibility due to reduced surface area in contact with the blood, and minimizes any hemodynamic effect. In some non-limiting aspects, the catheter shaft 22 can have a diameter of two (2) millimeters (mm) or six (6) French (Fr). In still other non-limiting aspects, the catheter shaft 22 (FIG. 1A) and the catheter shaft 222 (FIG. 2A) can have a diameter between one (1) mm and three (3) mm, or 3 Fr and 9 Fr. The diameters of the catheter 20 can be between approximately 1 mm to 16 mm. As explained in further detail below, in some examples, the catheter 20 can have a traveling or compressed state where the bundle of HFMs 34 are compacted together for the insertion and placement of the catheter 20 within a subject, and a deployed state where the HFMs 34 are expanded out for operation of the oxygenation system. In such examples, the catheter 20 may have a diameter of between 1 to 12 mm (3 and 36 Fr respectively) in the compressed state, and a larger diameter in the deployed state than in the compressed state. For example, the catheter may expand up to a diameter of 25 mm in the deployed state.

The catheter 20 is scalable such that it could be a small size appropriate for use in a neonate all the way up to a size appropriate for an adult. As such, it could range in size from one loop of HFM 34, to dozens of HFMs 34, to above 100 HFMs 34. For example, the number of HFMs 34 in the bundle of HFMs 34 can be in a range of between 1-400 HFMs, between 1-100 HFMs, between 100 and 200 HFMs, between 100 and 300 HFMs, between 200 and 300 HFMs, between 200 and 400 HFMs, between 300 and 400 HFMs, between 250 and 350 HFMs, etc.). In a non-limiting aspect, the catheter 20 of FIG. 1B may have nineteen (19) hollow fiber membranes 34 retained in the manifold 42 of the catheter shaft 22. In another non-limiting aspect, any appropriate number of HFMs 34 can be positioned in the catheter 20, for example between 1-400 HFMs, between 1-100 HFMs, between 100 and 200 HFMs, between 100 and 300 HFMs, between 200 and 300 HFMs, between 200 and 400 HFMs, between 300 and 400 HFMs, between 250 and 350 HFMs, etc., etc. can be located in the catheter 20.

In a non-limiting aspect, each individual HFM 34 can be 254 micrometers (μm) in diameter and have a wall thickness 25.4 In a non-limiting aspect, each individual HFM 34 can be between 200 and 800 micrometers (μm), including but not limited to, between 250 and 750 micrometers (μm), between 300 and 500 micrometers (μm), or between 350 and 450 micrometers (μm) in diameter and have a wall thickness between 20 and 30 In another non-limiting aspect, HFMs 34 can be 406.4 micrometers (μm) in diameter with a wall thickness of 88.9 micrometers (μm). In a non-limiting aspect, each individual HFM 35 can have a wall thickness of between 10 and 500 micrometers (μm), including but not limited to, between 25 and 400 micrometers (μm), between 50 and 250 micrometers (μm), or between 75 and 125 micrometers (μm). In other non-limiting aspect, the HFMs 34 can range from 200 micrometers (μm) to 1800 micrometers (μm) in diameter with wall thicknesses ranging from 25 micrometers (μm) to 300 micrometers (μm). Additionally, the HFMs 34 can be custom manufactured to have varying wall thickness. In some non-limiting aspects, the HFMs 34 can extend to a length of 10 cm or 30 cm in a direction parallel with the longitudinal axis 28 of the catheter 20. In some non-limiting aspects, the HFMs 34 can extend to a length between 5 cm and 20 cm or between 5 cm and 50 cm in a direction parallel with the longitudinal axis 28 of the catheter 20.

Additionally, in some examples, a total surface area of the HFMs 34 may be between 0.02 $m^2$ to 0.20 $m^2$, or a sub-range therein, such as 0.05 $m^2$ to 0.15 $m^2$, 0.07 $m^2$ to 0.13 $m^2$, 0.09 $m^2$ to 0.11 $m^2$, or the like.

Accordingly, because of the increased oxygen diffusion flux provided by the catheters 20 in the systems and methods described herein, the bundle of HFMs 34 of the various examples of catheters 20 provided herein may be substantially more compact, e.g., in terms of quantity of HFMs 34 (e.g., 33%, 50%, or more reduction) and in terms of surface area of the HFMs 34 (e.g., 66%, 83%, or more reduction), than other known systems, while still achieving desired oxygen transfer rates to a subject. In some examples, an oxygen transfer rate to a subject may be at or around 50 ml $O_2$/minute, although the particular rate may change depending on circumstances of a subject.

The catheter 20 may be flexible such that it can be inserted non-invasively to a region of interest in a subject. The catheter 20 is dimensioned for intravascular placement into a subject at bedside via a percutaneous approach to reach the region of interest. The catheter 20 is dimensioned for placement into the region of interest using an introducer sheath that can provide guidance for the catheter 20 to reach the region of interest. In a non-limiting example, the region of interest may be a large vessel such as the inferior vena cava, or the catheter 20 could be placed across the right atrium of the subject's heart. The catheter 20 can be placed peripherally (e.g. into the groin or neck) and maneuvered to a central venous location such as the inferior or superior vena cava or into the right atrium. The catheter 20 can also be positioned in the arterial side in select patients so that the catheter 20 could be positioned in the aorta. Additionally, the catheter 20 could be positioned in other regions of interest other than the vasculature such as intrathecal, intraperitoneal, or subcutaneously. As will be discussed in more detail below, catheter 20 may be manufactured from biocompatible material(s) and can be disposable. In some aspects, the catheter 20 can be placed surgically, for example, in the inferior or superior vena cava. The hyperbaric nature of the catheter 20 provides improved intravascular oxygenation via the pressure gradient between the HFMs 34 and the region (s) of interest discussed above.

As discussed above, the catheter 20 can be used for intravascular oxygenation of a region of interest in a subject by oxygenating the blood in a patient, which may be a critically ill patient with sick and failing lungs. The catheter 20 is dimensioned for insertion intravascularly and diffuses oxygen into the blood that flows past it due to the hyperbaric nature of the catheter 20 and oscillation of the HFMs 34, offloading much of the work of the patient's lungs and supporting the patient as the lungs heal from the underlying disease. The catheter 20 can maintain adequate oxygenation in patients with both acute and chronic lung diseases and can be an adjunct to mechanical ventilation (or could be used by itself) and may replace or delay the need for Extracorporeal Membrane Oxygenation. The Intravascular Membrane Oxygenator Catheter overcomes these limitations through a design that is easy to deploy, simple to use, and delivers a clinically significant amount of oxygen to the patient. In some aspects, the catheter 20 can deliver any amount of oxygen that could be useful to the patient. Accordingly, the catheter 20 may deliver at least 0.1 percent of the patient's oxygen needs. The catheter 20 may deliver between 0.1 percent and one percent of the patient's oxygen needs. In some aspects, the catheter 20 may deliver greater than one (1) percent of the patient's oxygen needs. For example, the catheter 20 may deliver one (1) percent to five (5) percent of the patient's oxygen needs. In some aspects, the catheter 20 may deliver five (5) percent to twenty-five (25) percent of the patient's oxygen needs. In some aspects, the catheter 20 may deliver twenty five (25) percent or more of a patient's basal oxygen needs in a catheter 20 configured to be sized to easily fit intravascularly into a region of interest. Furthermore, the catheter may deliver 50-100% of the patient's basal oxygen demand. In some cases, the catheter may deliver greater than 100% of the patient's basal oxygen demand.

Using known oxygen permeabilities and tensile strengths of various materials (e.g. polymers), a small bundle of HFMs 34, which may be equal or smaller in size than current central intravenous catheters, oscillated and placed under high pressures (for example, at or above 1.1 bar of absolute pressure, between 1.1 bar and 2 bar, or between 1.1 bar and 5 bar of absolute pressure) can diffuse a clinically significant amount of oxygen at well under the bursting pressures of the HFMs 34. In some examples, oxygenated gas is provided to the HFMs 34 at a pressure above or below the 1.1 bar to 2 bar range.

The catheter 20 (and HFMs 34) may include a traveling state with compressed HFMs 34 and a deployed state with deployed or expanded HFMs 34. For example, referring again to FIG. 2A, the catheter 20b can include a retractable sheath 235 that can compress the HFMs 34 during insertion and travelling to a region of interest. When the retractable sheath 235 surrounds and compresses the HFMs 34, the catheter 20b (and HFMs 34) is in a travelling state. During deployment, the retractable sheath 235 can be retracted in a proximal direction (away from a distal end of the HFMs 34) along the catheter shaft 222 to deploy the HFMs 34. In some embodiments, an expandable spacer 240 can be provided with the HFMs 34 and used to deploy the HFMs 34. For example, the expandable spacer 240 may be a spring that is compressed by the retractable sheath 235 when the catheter 20b is in the traveling state, and that expands due to the spring forces when the retractable sheath 235 is retracted. The expandable spacer 240 may further be coupled to one or more HFMs 34 to cause the expansion of the HFMs 34 as the spacer 240 expands.

Figure 2B:
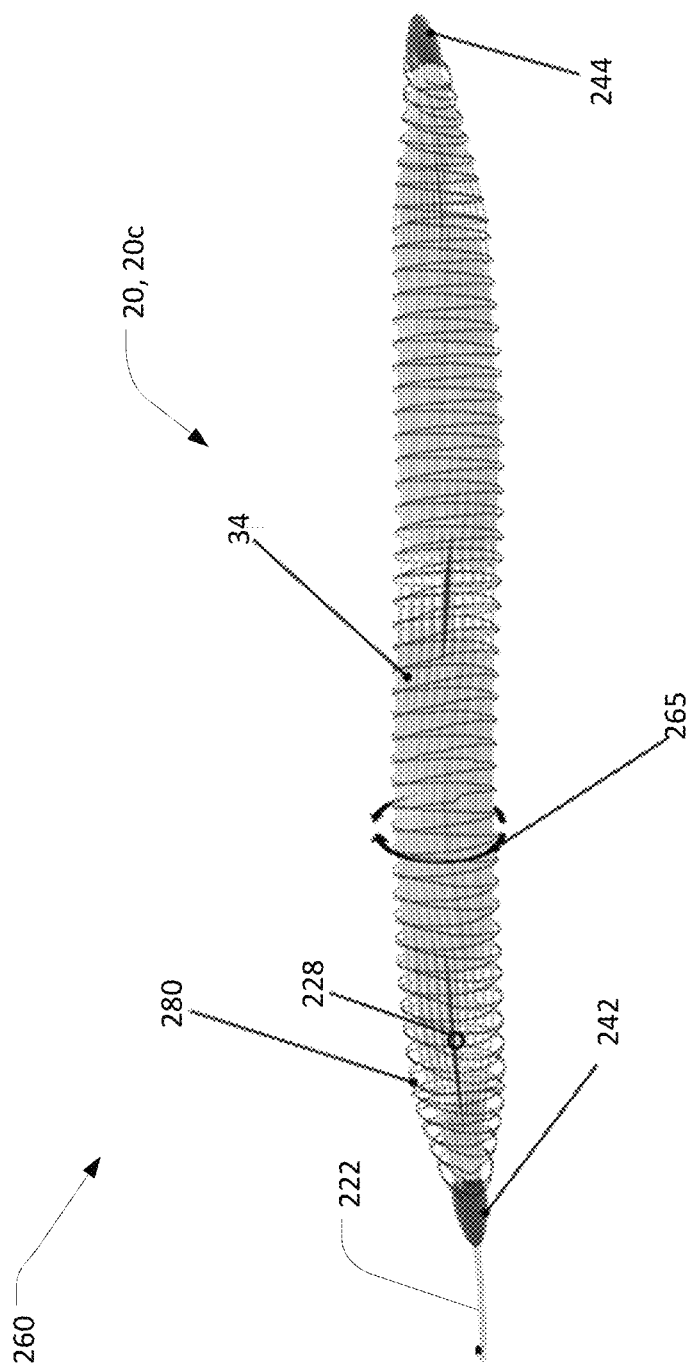
FIG. 2B is an illustration of another aspect of the intravascular oxygenation system of FIG. 2A with a protective guard.

Referring now to FIG. 2B, a catheter 20c is illustrated. The catheter 20c is similar to the catheter 20b of FIG. 2A in that the catheter 20c includes HFMs 34 in a non-looped arrangement and a central shaft 228 coupled between a proximal end tip 242 and a distal end tip 244. The catheter shaft 222 may, similar to FIG. 2A, include a drive shaft 11 coupled to a motor 10, and an inlet 236 and outlet 238 coupled to a pneumatic control system 50, and each may be configured and function as described above with respect to FIG. 2A. Thus, the catheter 20c of FIG. 2B may be used in the system 200 of FIG. 2A in place of the catheter 20b and/or in the system 100 of FIG. 1A in place of the catheter 20a. In the illustration of FIG. 2B, the proximal and distal end tips 242 and 244 retaining and providing pneumatic connections for the HFMs 34 and central shaft 228 are more pronounced. Such end tips may also be present in the catheter 20b of FIG. 2A. Although not shown in FIG. 2B, the catheter 20c may also be provided with a retractable sheath 235 such as described with respect to the catheter 20b, which may similarly define a traveling state and deployed state for the catheter 20c.

The catheter 20c of FIG. 2B further includes a protective guard 280. The protective guard 280 also extends between (and has ends retained by) the proximal end tip 242 and the distal end tip 244. The protective guard may be, for example, a wire mesh cage, a self-expanding stent comprising nitinol, a semipermeable sheath, or a balloon-expandable stent. The protective guard 280 may surround or contain the HFMs 34. In some examples, proximal end tip 242 and the distal end tip 244 may each include a static portion and a rotatable portion that may rotate relative to one another. For example, the portions may be coupled by a bushing to enable the relative rotation. The protective guard 280 may be coupled to and retained by the static portion, while the drive shaft 11 and the HFMs 34 may be coupled to and retained by the rotatable portion. Accordingly, the protective guard 280 and static portion of the end tips 242 and 244 may remain stationary while the HFMs 34 and rotatable portions of the end tips 242 and 244 are rotated or oscillated by the motor 10 via drive shaft 11 (e.g., as indicate by oscillations 265).

In some alternate examples, the protective guard would be part of a separate stent that is inserted into a region of interest (a vasculature) of a subject first, and then catheter 20 with HFM bundle 34 are inserted into the protective guard. The bundle of HFMs 34 may then be deployed (expanded), if inserted in a compressed state, and then oscillated according to the various techniques described herein. Accordingly, in these embodiments, the protective guard may not be physically coupled to the HFM bundle 34 within the region of interest. In some examples, having the protective guard inserted separately from the bundle of HFMs 34 provides a reduced insertional size for the oxygenation system.

Figure 2C:
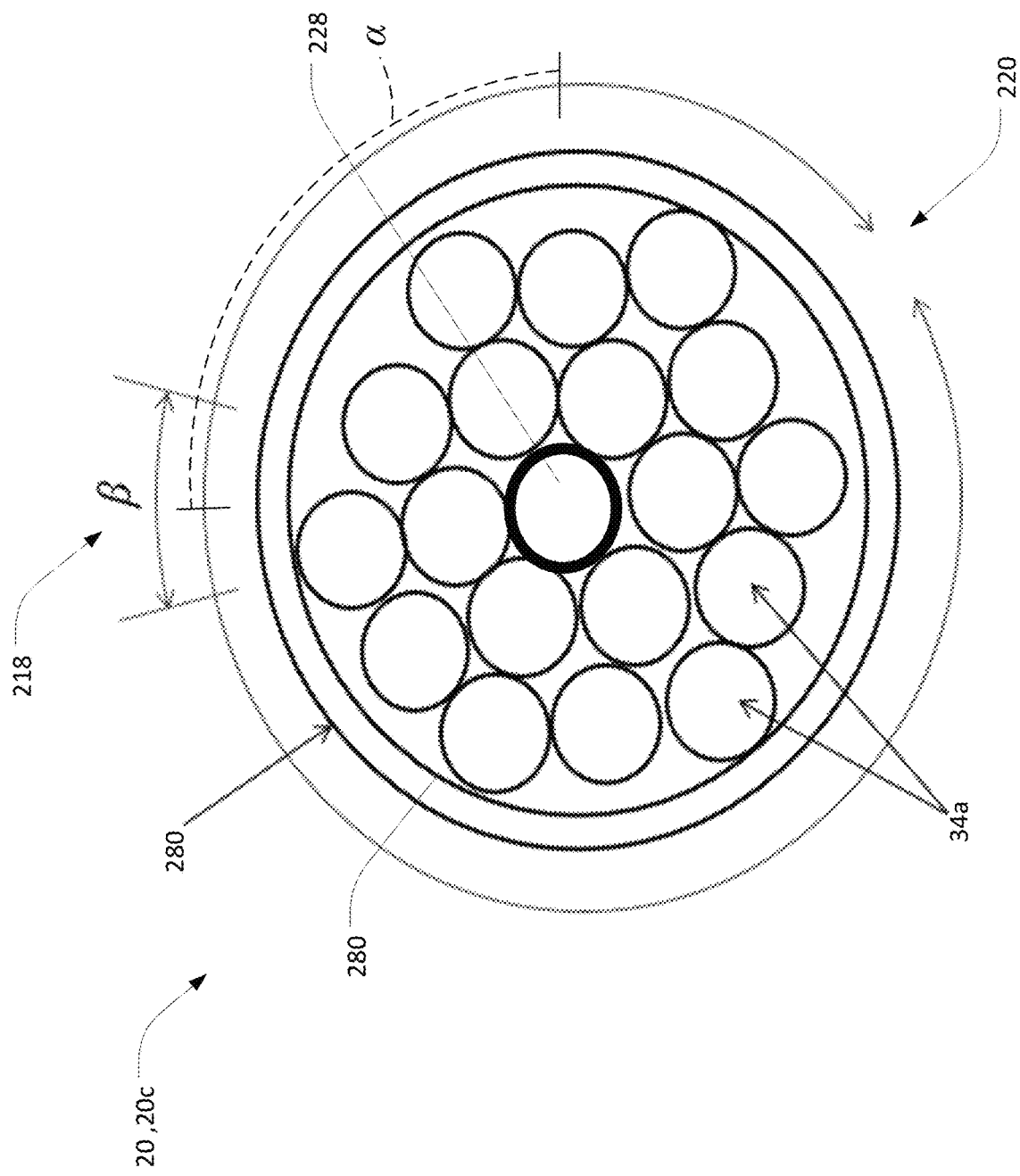
FIG. 2C is a cross-sectional view of the intravascular oxygenation system of FIG. 2B with a protective guard

FIG. 2C shows a cross-sectional view of the catheter 20c shown in FIG. 2B. The bundle of HFMs 34 is illustrated within protective guard 280 in a (compressed) traveling state, although the retractable sheath 235 providing the compression is not illustrated. The bundle of HFMs 34 is illustrated as included eighteen HFMs, two of which are labeled HFMs 34a. The central shaft 228 is also illustrated within the catheter shaft 222. However, the particular number of HFMs within the bundle of HFMs 34 may vary (e.g., between 100 and 200 HFMs, between 100 and 300 HFMs, between 200 and 300 HFMs, etc., as described above). FIG. 2C also illustrates examples of oscillations resulting from driving of the motor 10, including macro-oscillations 220 and micro-oscillations 218. In the example embodiment of FIG. 1B, the macro-oscillations 220 are in the range of approximately 360°, with α representing an example step of the macro-oscillations 120 of approximately 90 degrees, and β represents the micro-oscillations in the range of approximately 15°. However, the macro-oscillations 120 for the system 100 may be in the range of approximately 1-360° (or a narrower range, such as 22.5-360°, 22.5-180°, 45-180°, or 90-180°, etc.), with steps α of the macro-oscillation 120 being in a range of 1-360 (or a narrower range, such as 22.5-360°, 22.5-180°, 45-180°, or 90-180°, etc.), and the micro-oscillations may be in the range of approximately 1-180° (or a narrower range, such as 5-45°, 15-30°, 22.5-45°, 30-90°). In some examples, macro-oscillations or micro-oscillations of the bundle of HFMs 34, but not both, are provided in the system 200. Further description of various techniques for oscillating the bundle of HFMs 34 is provided below.

In some examples, in place of or in addition to a retractable sheath, such as the retractable sheath 235, the HFMs 34 may be wound around a central shaft, such as the central shaft 228, to place the catheter 20 in compressed state. For example, to wind the HFMs 34, the distal end 244 may be rotated in a first direction while the proximal end 242 is stationary. Then, to place the catheter 20 in the deployed state, the HFMs 34 may be unwound. For example, to unwind the HFMs 34, the distal end 244 may be rotated in a second direction (opposite the first direction). The unwinding force may be provided by conversion of potential energy stored in the wound HFMs 34 (e.g., serving as a spring) to kinetic energy. In some examples, the retractable sheath 235 maintains the HFMs 34 in a wound state, and retracting of the retractable sheath 235 may cause the HFMs 34 to unwind to the deployed state.

Figure 3A:
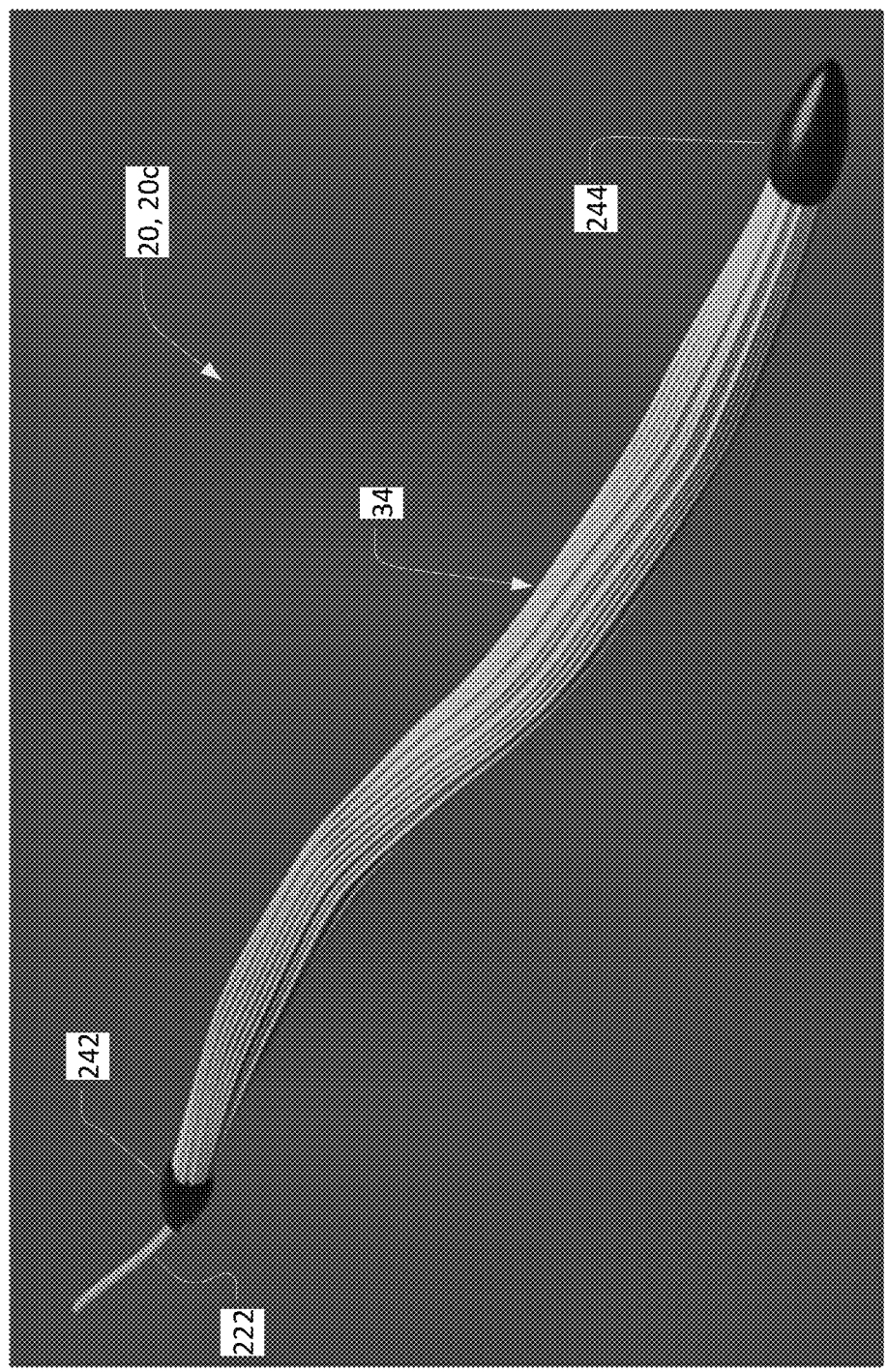
FIG. 3A shows a perspective view of the catheter of FIG. 2C without a protective guard and in a compressed configuration.
Figure 3B:
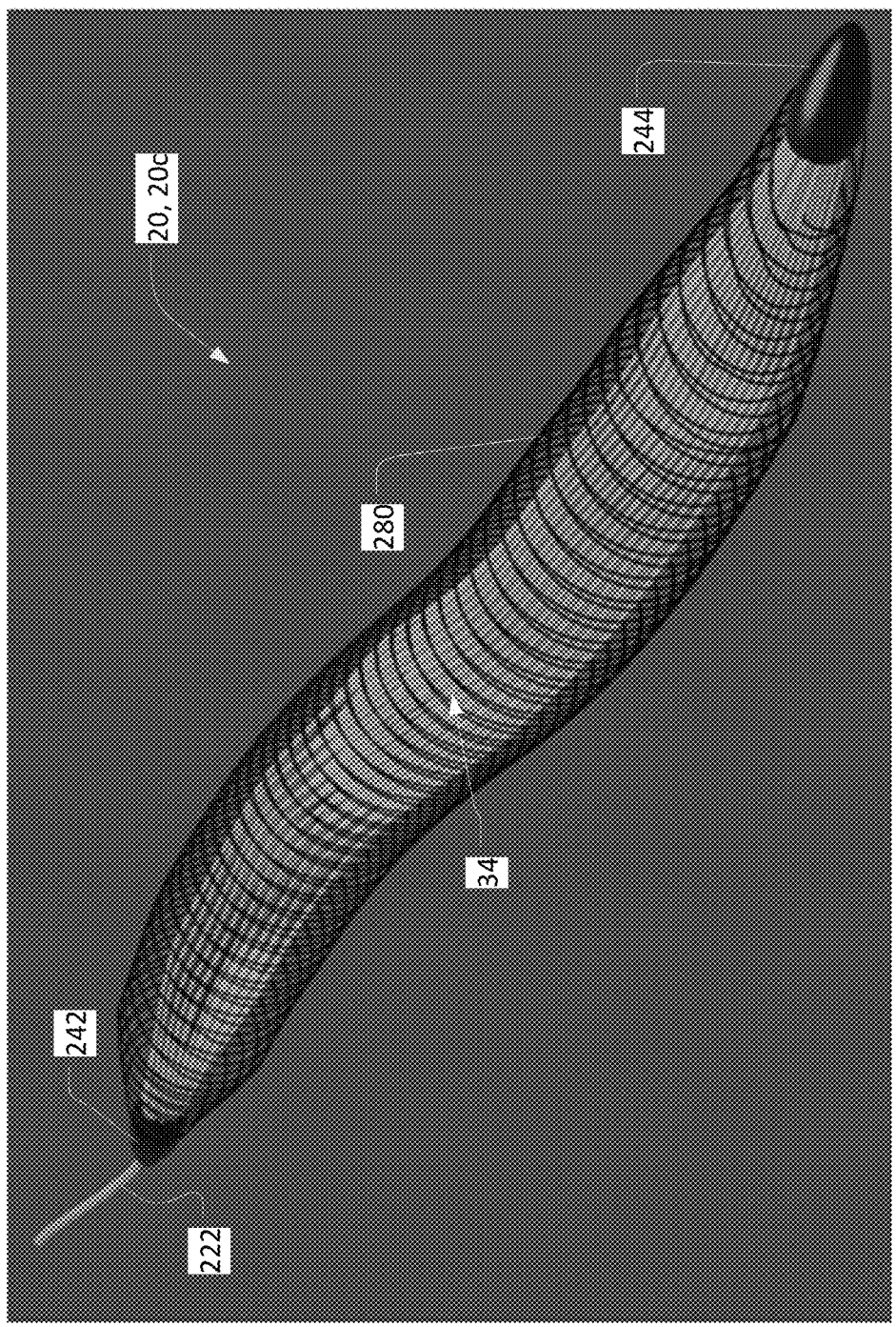
FIG. 3B shows a perspective view of the catheter of FIG. 2C in a deployed configuration.

Referring now to FIG. 3A, a compressed travelling state conformation of the HFMs 34 (without guard 280) of the catheter 20c is shown. In some embodiments, the HFMs are compressed by a retractable sheath 235 (not shown), which defines a travelling state conformation. Referring now to FIG. 3B, a deployed state conformation of the HFMs 34 (with guard 280) of the catheter 20c is shown. Retracting the retractable sheath 235 can release the HFMs 34 and define the deployed state. In some examples, a protective guard 280 surrounds the HFMs 34 in the travelling state conformation, the deployed state conformation, or both conformations.

Figure 4A:
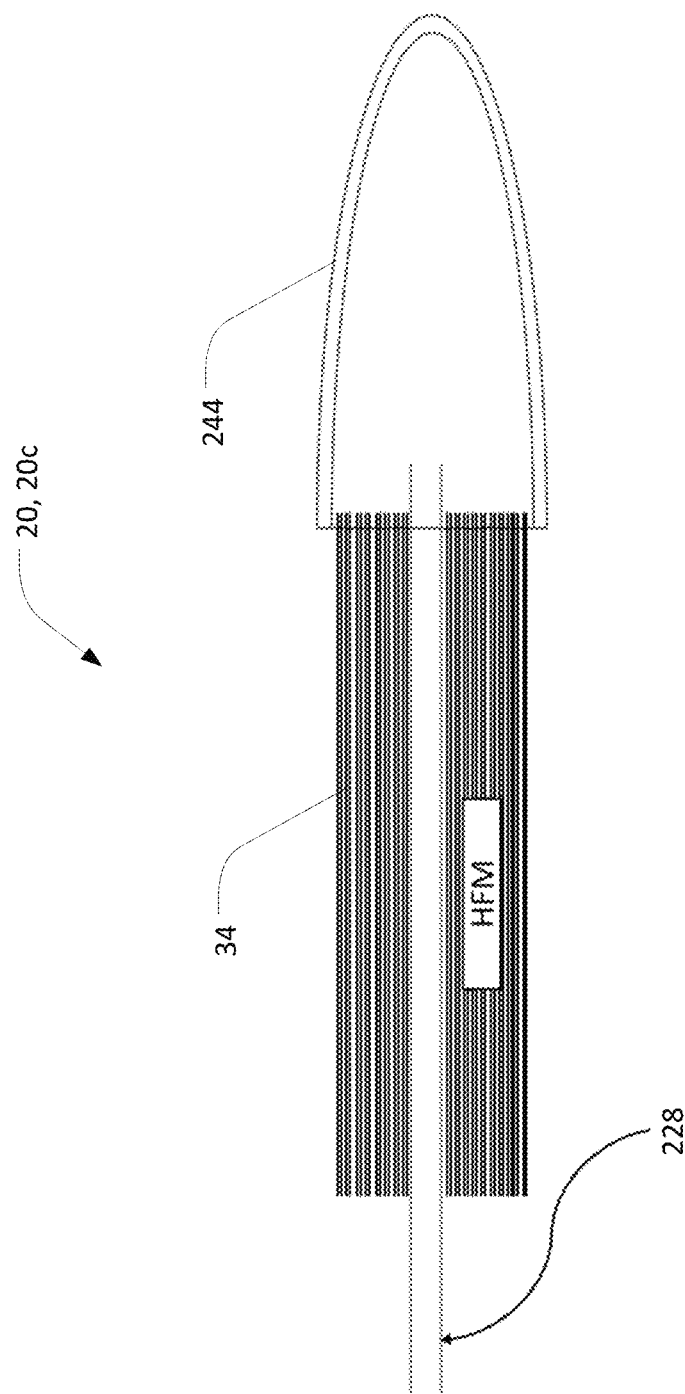
FIGS. 4A and 4B illustrate a magnified view of a distal end of the catheter of FIG. 2B in a compressed state and a deployed state, respectively.
Figure 4B:
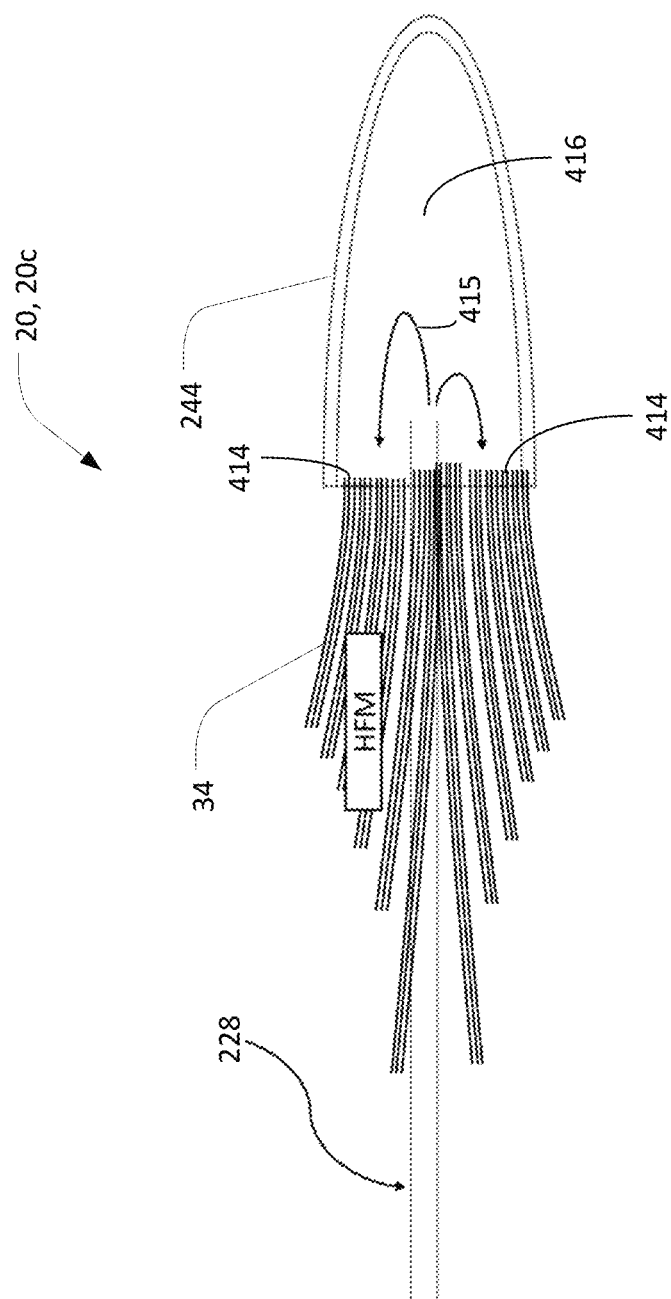

FIGS. 4A-4B illustrate a magnified view of a distal end of the catheter 20c of FIG. 2B in a traveling (compressed) state and a deployed (expanded) state, respectively. Referring now to FIG. 4A, the HFMs 34 are in the traveling state, and only a portion of the length of the HFMs 34 are illustrated (rather than the full length of the HFMs 34). As described above, the HFMs 34 and central shaft 228 can be retained by the distal end tip 244. Referring now to FIG. 4B, the HFMs 34 are in a deployed state and only a portion of the length of the HFMs 34 are illustrated (rather than the full length of the HFMs 34). In operation, the gas containing oxygen (also referred to as oxygenated gas), identified as gas 415 in FIG. 4B, may travel through the central shaft 228 to the distal end tip 244 and be exhausted from the central shaft 228 into the distal end tip 244. The oxygenated gas 415 can then be received by inlets 414 of each of the HFMs 34 through an air channel or volume 416 defined by the distal end tip 244. The oxygenated gas 415 then travels in a proximal direction (towards the proximal end tip 242, see FIG. 2C) from the distal end tip 244 through the HFMs 34. In some embodiments, the inlets 414 are configured to receive the gas in the distal end tip 244 through a vacuum created by a pneumatic control system, thereby pulling the gas through the inlets 414 of the HFMs 34.

Figure 5:
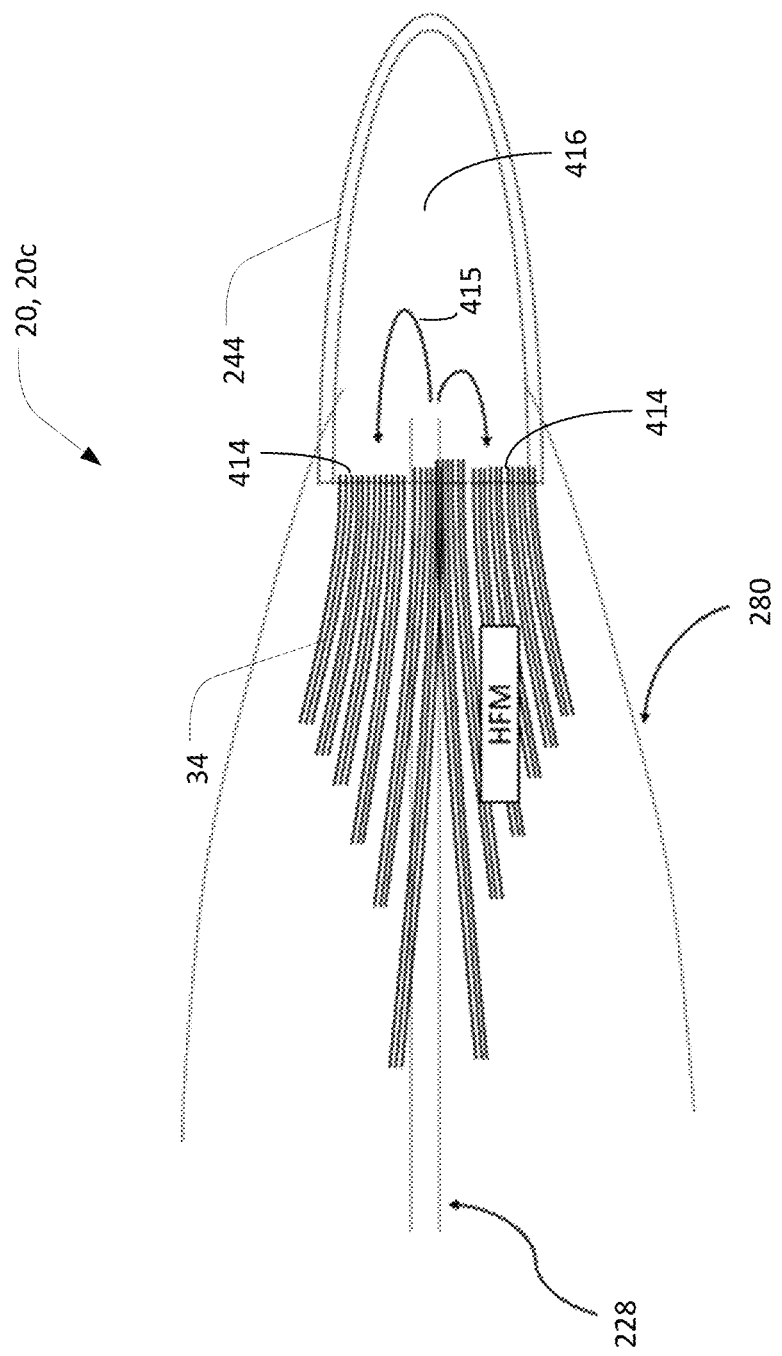
FIG. 5 illustrates another magnified view of the distal end of the catheter of FIG. 2B with a protective guard.

FIG. 5 illustrates another magnified view of the distal end of the catheter 20c of FIG. 2B, similar to FIG. 4B, except that the protective guard 280 is also illustrated.

Figure 6:
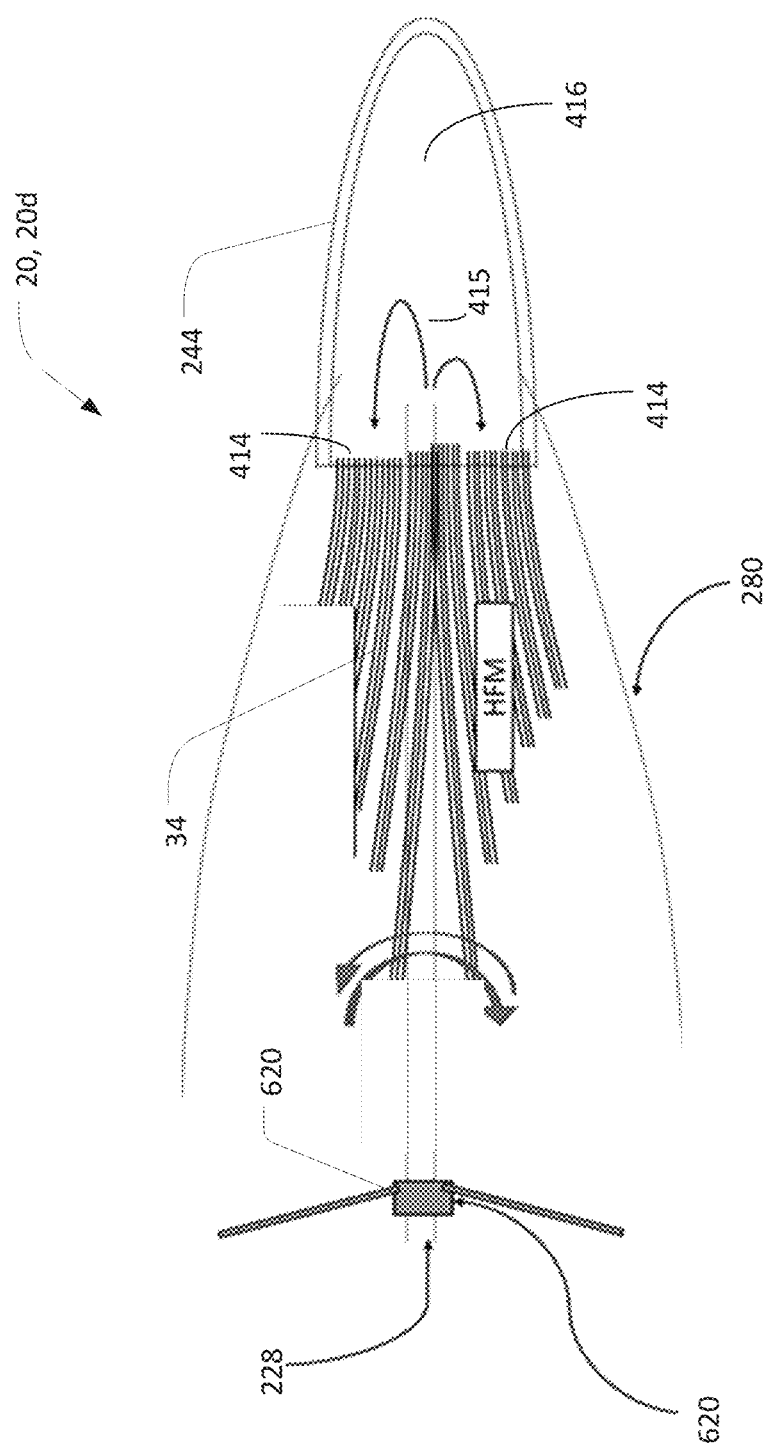
FIG. 6 illustrates a magnified view of a distal end of a catheter according to another embodiment including an independent rotational device.

FIG. 6 illustrates a magnified view of a distal end of a catheter 20d, which is another embodiment of the catheter 20. The catheter 20d may be similar to the catheter 20c, except for any differences noted herein. The catheter 20d that includes an independent rotational device 620 (e.g., a miniaturized motor or oscillator) connected to the central shaft 228. The independent rotational device 620 can oscillate the HFMs 34 to. This device 620 may also be capable of compressing to fit inside of the bundled HFMs in the compressed state configuration prior to deployment. In some embodiments, the oxygenation system 100 or 200 includes the catheter 20d with independent rotation device 620 in place of the motor 10 and drive shaft 11 to oscillate the HFMs 34.

Figure 7A:
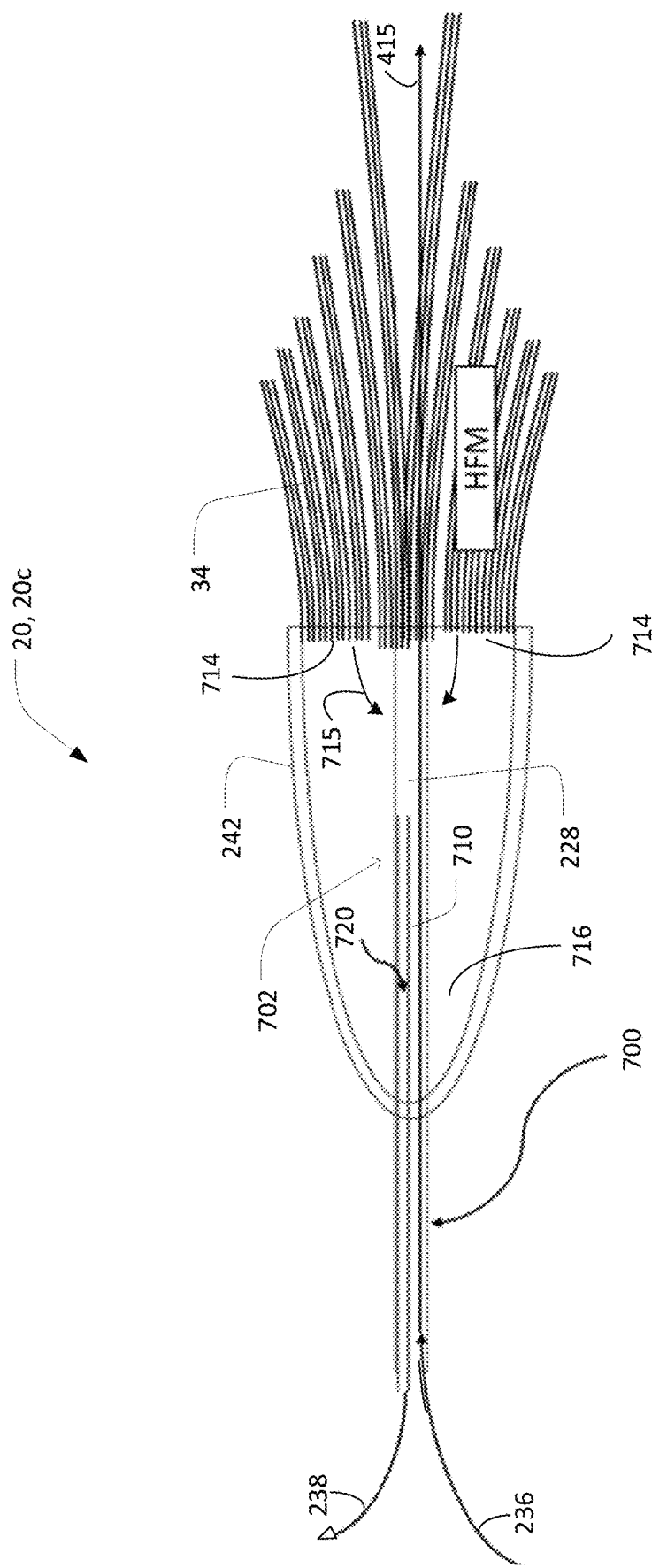
FIG. 7A illustrates a magnified view of a proximal end of the catheter of FIG. 2B.

FIG. 7A illustrates a magnified view of a proximal end of the catheter 20c of FIG. 2B. In this view, a double lumen 700 of a proximal section 702 of the central shaft 228 is shown. The proximal section 702 of the central shaft 228 can be understood to include the portion of the central shaft 228 that is disposed within the proximal end tip 242 of the oxygenation system 200 and that connects to the pneumatic inlet 236 and pneumatic outlet 238. The double lumen 700 of the central shaft 228 includes an inflow lumen 710 pneumatically coupled to the pneumatic inlet 236 and extending through the central shaft to the distal end tip 244 to pneumatically couple to the HFMs 34 (see, e.g., FIG. 5). The double lumen 700 further includes an outflow lumen 720 pneumatically coupled to the distal ends of the HFMs 34 at the proximal end tip 242. For example, the outlets (or distal ends) 714 of the HFM 34 may exhaust deoxygenated gas 715 into an air channel or volume 716 defined by the proximal end tip 242. The deoxygenated gas 715 may then be received the outflow lumen 720. Accordingly, the inflow lumen 710 is configured to receive a high-pressure gas 415 containing oxygen from the pneumatic inlet 236 and transport the gas 415 to inlets of the HFMs 34 at the distal end tip 244. The outflow lumen 820 is configured to receive deoxygenated gas 715 from the outlets of the HFMs 34 at the proximal end tip 242 and transport the deoxygenated gas 715 to the pneumatic outlet 238.

Figure 7B:
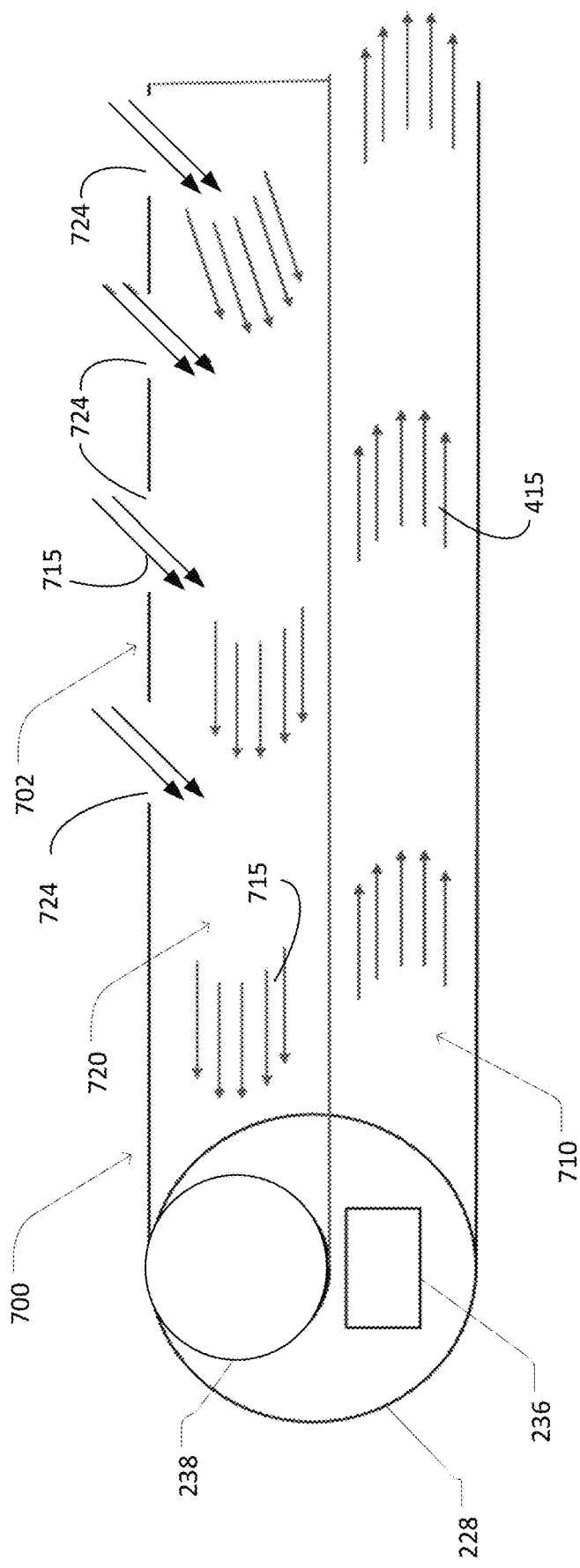
FIG. 7B is a schematic diagram of a double lumen central shaft exchanging gas in an oxygenation system.

FIG. 7B illustrates a schematic diagram of the double lumen 700 of the proximal section 702 of the central shaft 228. As described with respect to FIG. 7A, the inflow lumen 710 can extend the entire length of the central shaft 228 defined between the proximal end tip 242 and distal end tip 244. The outflow lumen 720 can extend alongside the inflow lumen along a length confined within the proximal end tip 242. However, the outflow lumen 720 can also extend the entire length of the central shaft 228 in certain aspects. The outflow lumen 720 can be connected to each outlet of the HFMs 34, or the outflow lumen 720 can be connected to a fluid channel disposed within the proximal end tip 242 that places the outflow lumen 720 in fluid communication with the outlets of the HFMs. For example, the outflow lumen may include one or more openings 724 (see FIG. 7A) in fluid communication with the volume 716 of the proximal end tip 242 (see FIG. 7B) to receive the outflow of deoxygenated gas 715 from the outlets of the HFMs 34.

As noted above, in some examples, the catheter 20c is designed such that the flow path of the gas is reversed, in which case the lumen 720 may be an inlet that provides an inflow of gas received from the pneumatic inlet 236 to the proximal end of the HFMs 34, and the lumen 710 may be an outlet that receives an exhaust of deoxygenated gas from the distal ends of the HFMs 34 and transports the deoxygenated gas along the length of the central shaft 228 back to the pneumatic outlet 238.

Figure 7C:
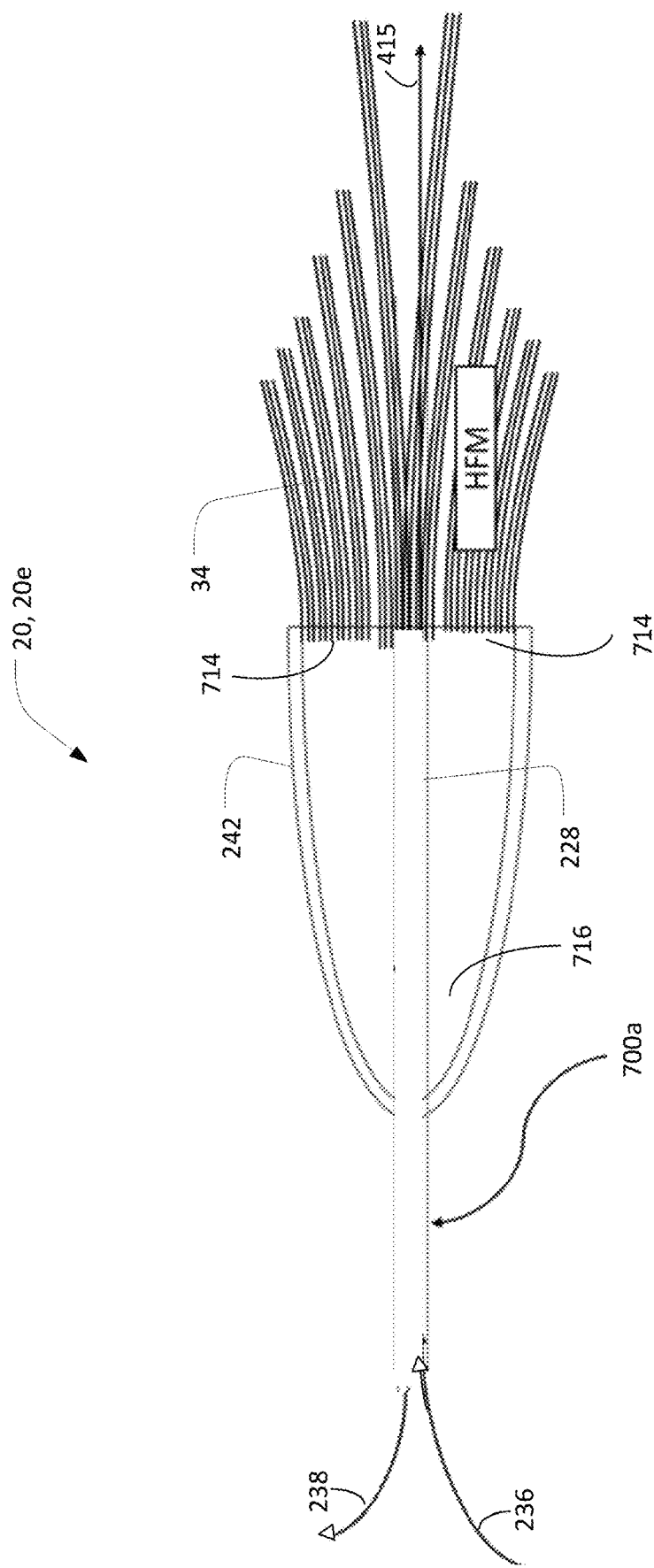
FIG. 7C is a magnified view of a proximal end of a catheter with a shared lumen in an oxygenation system according to some embodiments.

FIG. 7C illustrates a magnified view of a proximal end of a catheter 20e. The catheter 20e may also be used in some examples of the system 200. The catheter 20e may be similar to the catheter 20c except for the differences noted herein. In particular, instead of having an inflow lumen and an outflow lumen coupled to the inlet 236 and outlet 238, respectively, the catheter 20e has one shared lumen 700a coupled to both the inlet 236 and the outlet 238 that serves as both inlet and outlet to the HFMs 34 in a time-multiplexed fashion. In particular, a lumen 700a of the central shaft 228 is connected to both the outlet 238 and inlet 236. The lumen 700a may be pneumatically coupled to the HFMs 34 either at the proximal end tip 242 shown in FIG. 7C, or at a distal end tip of the catheter 20e (see, distal end tip 244 of FIG. 5). In operation, the system 200 (e.g., the pneumatic control system 50 under control by the electronic processor 12) performs a cyclic process of filling and draining the HFMs 34 with oxygenated gas through the shared lumen 700a. For example, the system 200 fills the HFMs 34 with oxygenated gas under pressure through the shared lumen 700a (serving as an inlet) and holds the gas at the pressure for a set amount of time. Then, the system 200 generates a vacuum (e.g., using vacuum system 237) to pull out the oxygenated gas (and back-diffused water vapor) from the HFMs 34 through the shared lumen 700a (now acting as an outlet). The system 200 then restarts the cyclic process to continually fill, hold, and pull oxygenated gas in the HFMs 34. With a shared orifice and lumen, the catheter 20e may have a less complex construction than other catheters 20 having distinct inlet and outlets.

Figure 8:
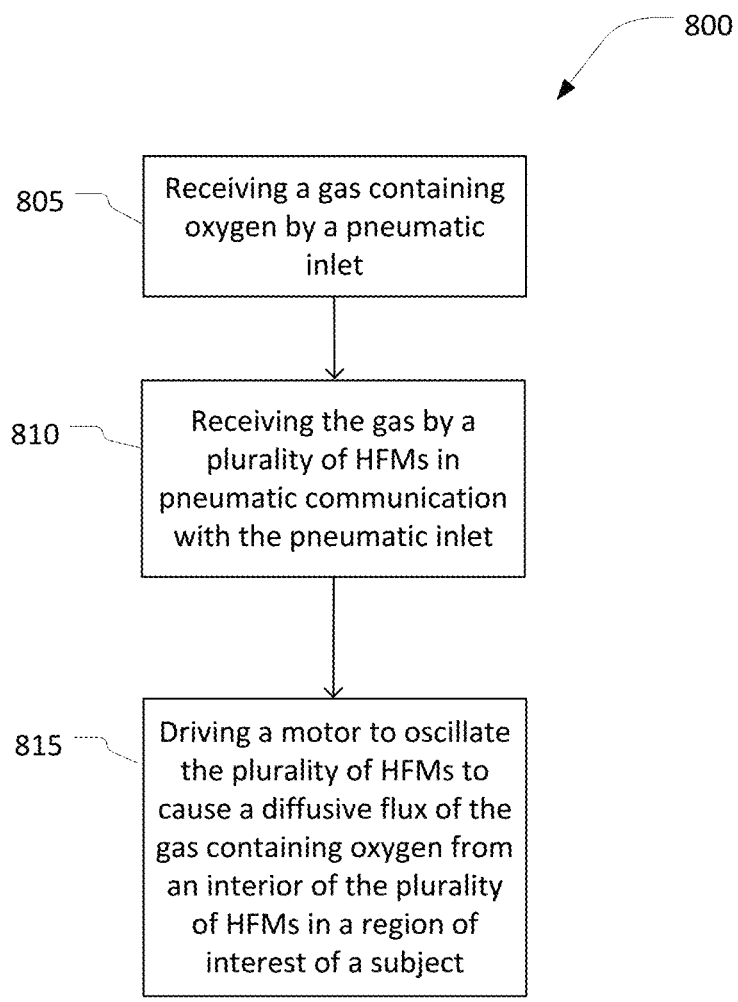
FIG. 8 is a flow chart of a method of intravascular oxygenation.

FIG. 8 illustrates a flowchart of a process 800 for intravascular oxygenation, which can be implemented using any of the systems described herein. For example, the process 800 may be implemented with the system 100, the system 200, any of catheters 20 (e.g., catheters 20a, 20b, 20c, or 20d), as well as by variations of these systems and other systems having additional components, fewer components, alternative components, or the like. Additionally, although the blocks of the process 800 are illustrated in a particular order, in some embodiments, one or more of the blocks can be executed partially or entirely in parallel, can be executed in a different order than illustrated in FIG. 8, or can be bypassed. For illustration purposes, the process 800 is generally described as being implemented by the oxygenation system 200 with catheter 20c (see, e.g., FIGS. 2A-5, 7A, and 7B).

In block 805, a pneumatic inlet coupled to a pneumatic source receives a gas containing oxygen at a pressure at or above 1.1 bar of absolute pressure. For example, with reference to FIG. 2A, the pneumatic inlet 236 may receive a gas containing oxygen (also referred to as oxygenated gas) 415 from the pneumatic source 32 via pneumatic control system 50. In some examples, as described above, the electronic controller 12 may control the pneumatic source 32 and/or the pneumatic control system 50 to provide the oxygenated gas 415 (and regulate the oxygenated gas 415 to be at) a particular pressure (e.g., at or above 1.1 bar of absolute pressure), a particular temperature, and/or a particular flow rate. For example, the particular pressure, temperature, and/or flow rate of the oxygenated gas 415 may be based on clinician input received by the electronic controller 12 via a user interface thereof (e.g., a touch screen, dials, knobs, etc.). That is, the clinician input may include target pressure, temperature, and/or flow rate of the oxygenated gas 415, and the electronic controller 12 may then regulate the target pressure, temperature, and/or flow rate of the oxygenated gas 415 to be provided at the target pressure, temperature, and/or flow rate (within certain acceptable tolerances). The electronic controller 12 may regulate these characteristics of the oxygenated gas 415 via control of one or more valves (to control pressure and flow rate) and one or more heating or cooling devices (to control temperature) of the pneumatic control system 50 and/or pneumatic source 32. This control may be based on one or more sensor outputs received by the electronic controller 12 indicating one or more of the pressure, temperature, and flow rate at, for example, the inlet 236 and outlet 238.

In block 810, a plurality of hollow fiber membranes (HFMs) in pneumatic communication with the pneumatic inlet receive the gas containing oxygen. For example, the bundle of HFMs 34 may be in communication with the pneumatic inlet 236 and receive the oxygenated gas 415 from the pneumatic inlet 236. For example, with reference to FIG. 7A, the pneumatic inlet 36 may be coupled to the inflow lumen 710 of the double lumen 800 of the central shaft 228. With reference to FIG. 4B, the inflow of the oxygenated gas 415 may be transported by the central shaft 228 (through the inflow lumen 710) to the distal tip end 244. The oxygenated gas 415 may then be received by the inlets 414 of the HFMs 34, as described with respect to FIG. 4B. In other examples, the flow may be reversed, and the inlet 236 is pneumatically coupled to distal ends of the HFMs 34 at the distal end tip 244 to receive the oxygenated gas 415.

In block 815, an electronic controller drives a motor to oscillate the plurality of HFMs to cause a diffusive flux of the gas containing oxygen from an interior of the plurality of HFMs in a region of interest of a subject. For example, the electronic controller 12 may drive the motor 10 to oscillate the HFMs 34 according to one or more oscillation patterns. Oscillation patterns may include macro-oscillations, micro-oscillations, or a combination of macro- and micro-oscillations. Examples of oscillation patterns are discussed further below. The oscillation may be one cause of a plurality of causes for the diffusive flux of the gas (e.g., the construction of the HFMs, the hyperbaric pressure of the gas containing oxygen in the HFMs, etc.). Accordingly, in some examples, the diffusive flux referred to in block 815 may be considered the total diffusive flux resulting from the overall system and its operation (as the oscillations contribute to causing this overall diffusive flux), or may be considered the increase in diffusive flux attributable to the oscillation of the HFMs 34.

The oscillation of the HFMs 34 ultimately increases the diffusive flux of the gas into the region of interest from the HFMs 34, relative to static HFMs 34 or unidirectionally or constantly rotating HFMs 34. For example, oscillation causing the movement of HFMs in a direction perpendicular to blood flow can create a higher effective shear flow that reduces the opportunity for bubble formation. Additionally, oscillating the HFMs can increase convective mixing of the blood and increase the relative velocity of blood flowing past the HFM, which can reduce liquid boundary layer formation. These mechanisms both serve to reduce bubble formation and increase oxygen flux. Also, oscillations can induce movement such that the HFMs may have less opportunity for fiber-to-fiber contact in the vascular path, which could otherwise reduce efficiency. Further, the oscillations may induce vibrations along the fiber, and/or the motion of the oscillator can also directly or indirectly create a longitudinal wave along the length of the HFM, either or both of which may dislodge microscopic bubbles before they grow in size, increase convective mixing and reduce liquid boundary layer formation.

Additionally, with the increase in diffusive flux provided by the oscillations, the pressure of the oxygenated and deoxygenated gas in the catheter 20 and HFMs 34 may be reduced, relative to a system attempting to achieve similar diffusive flux rates that does not include oscillations. Moreover, the pressures required in a non-oscillating system to achieve similar diffusive flux may be too high and outside of an acceptable operation range of the HFMs or system. In other words, the oscillation of the HFMs 34 enables the system 200 (and 100) to achieve diffusive flux and higher rates than possible with non-oscillating (static or unidirectionally or constantly rotating) HFMs.

To oscillate the HFMs 34, the motor 10 may be coupled via a drive shaft 11 to the HFMs 34, as described above (e.g., with respect to FIGS. 2A-2B). Further, the electronic controller 12 may be programmed with one or more oscillation profiles, each profile associated with an oscillation pattern. Each oscillation profile may encode the oscillation pattern for the motor 10 to implement. Accordingly, the profile may include one or more of rotation angles (indicating an amount of rotation for an oscillation), angular positions (about which oscillations are to occur), rotation speeds (for a particular oscillation and/or for transiting between angular positions), and the like to define the movements of the motor 10 that make up an oscillation pattern. In some examples, one or more of these angles, positions, and speeds of one or more of the oscillation profiles may be pre-configured (e.g., at the time of manufacture or firmware update). In some examples, one or more of these angles, positions, and speeds of one or more of the oscillation profiles may be configurable, for example, by a clinician. For example, the oscillation profiles may be stored in the memory 16 of the electronic controller 12 and associated with an identifier (e.g., a name). A particular oscillation profile may be selected and/or configured based on clinician input received by a user interface of the electronic controller 12. In some examples, the clinician input includes a selection of a particular oscillation profile and/or configuration information indicative of the angles, positions, or speeds to be used for the profile. In other examples, the clinician input includes desired oxygenation characteristics. The electronic controller 12 may, in turn, select an oscillation profile and/or configuration of an oscillation profile associated with such oxygenation characteristics. Accordingly, based on a clinician input requesting an increase in the oxygenation of a region of interest, the electronic controller 12 may select a new oscillation profile and configuration, and/or modify a configuration of a current oscillation profile, that results in an increase in oxygenation (i.e., an increase in the diffusion flux). Similarly, based on a clinician input requesting a decrease in the oxygenation of a region of interest, the electronic controller 12 may select a new oscillation profile and configuration, and/or modify a configuration of a current oscillation profile, that results in a decrease in oxygenation (i.e., a decrease in the diffusion flux). In some examples, each oscillation profile may be associated with an oxygenation capability (e.g., defined as a ranking or score (e.g., 1-10) or with an average, maximum, and/or minimum oxygenation rate), a risk of hemolysis (or bubble formation) (e.g., defined as a ranking or score (e.g., 1-10) or another metric), and/or other characteristics. Accordingly, some oscillation profiles may be associated with higher oxygenation levels, but also with an increased risk of hemolysis (or bubbles), relative to other oscillation profiles. Nevertheless, in certain scenarios, a clinician may select such an oscillation profile, at least temporarily, taking into consideration the risk/benefit of treatment and the particular situation of a subject.

Accordingly, the electronic controller 12 may select and retrieve the oscillation profile (e.g., based on clinician input, pre-configuration, or otherwise). The electronic controller 12 may then translate the oscillation profile to motor drive commands (e.g., a series of commands to rotate the motor 10 clockwise and counterclockwise particular amounts and at particular speeds) and provide the motor drive commands to the motor 10 to achieve the oscillation pattern associated with the profile. In other words, the electronic controller 12 may employ standard motor driving techniques to drive the motor 10 to achieve the oscillation patterns.

Referring now to FIGS. 9A-9D, an oscillation pattern 900 is illustrated. The oscillation pattern 900 may be implemented by the electronic controller 12 (driving the motor 10) to oscillate the HFMs 34, for example, to implement block 815 of the process 800. The oscillation pattern 900 is an oscillation pattern without superimposed oscillations (such as described below). In FIGS. 9A-9D, a rotation axis 905 may represent a drive shaft 11 or center axis of the HFMs 34 (e.g., the central shaft 228), and the HFM 910 may represent a single HFM within the HFMs 34. Additionally, the other HFMs within the HFMs 34 may be presumed to rotate similarly to the HFM 910 (although each is offset from the HFM 910 and will have a unique position during the oscillations). As illustrated, the oscillation pattern 900 includes an oscillation of 180 degrees, made up of steps ($\alpha$) of 90 degrees. That is, the axis 905 (and HFM 910) rotates 90 degrees clockwise from a position 1 to position 2 in FIG. 9A, rotates 90 degrees clockwise from position 2 to a position 3 in FIG. 9B, rotates 90 degrees counterclockwise from position 3 to position 4 in FIG. 9C, and rotations 90 degrees counterclockwise from position 4 to position 5 in FIG. 9D. In some examples, the electronic controller 12 may repeat the pattern of FIGS. 9A-9D, causing the axis 905 (and HFM 910) to continue to oscillate 180 degrees from position 1 to position 3. In some examples, the motor 10 may pause the rotation of the axis 905 at each position 1, 2, 3, 4, and 5 before continuing to rotate the axis 905 to the next position. In some examples, the motor 10 does not pause at each position (but for an inherent pause to reverse direction at positions 1, 3, and 5). In some examples, the oscillation pattern 900 is modified to have an oscillation of more than 180 degrees or less than 180 degrees (e.g., a value between 5 and 360 degrees, between 5 and 180 degrees, between 5 and 90 degrees, between 5 and 22.5 degrees, between 22.5 and 45 degrees, etc). The steps α may also be referred to as oscillation steps or increments.

Referring now to FIGS. 9E-9H, an oscillation pattern 915 is illustrated with respect to the rotation axis 905 and HFM 910. The oscillation pattern 915 may be implemented by the electronic controller 12 (driving the motor 10) to oscillate the HFMs 34, for example, to implement block 815 of the process 800. The oscillation pattern 900 is an oscillation pattern with superimposed oscillations including macro-oscillations and micro-oscillations occurring at steps of the macro-oscillations. As illustrated, the oscillation pattern 915 includes a macro-oscillation of 180 degrees, made up of steps (α) of 90 degrees, and micro-oscillations of approximately 22.5 degrees. Specifically, FIG. 9E shows a 90-degree clockwise rotation of the rotation axis 905 (and HFM 910) from position one to position two. FIG. 9F shows an example of micro-oscillations of an angle β centered at position 2, as indicated by the directional arrows. FIG. 9G shows a 90-degree clockwise rotation of the rotation axis 905 (and HFM 910) from position two to position three. FIG. 9H shows another example of micro-oscillations of the angle β centered at position 3, as indicated by the directional arrows. To complete the macro-oscillation, the motor 10 further rotates the rotation axis 905 (and HFM 910) to rotate back to position 1. In some examples, the motor 10 rotates the axis 905 counterclockwise 180 degrees directly back to position 1 without additional steps α (e.g., without stopping at position 2). In other examples, the motor 10 rotates the axis 905 (and the HFM 910) counterclockwise a step α (e.g., 90 degrees) back to position 2, and the oscillates the rotation axis 905 (and HFM 910) to cause micro-oscillations of the angle β at position 2, before continuing on to return to position 1. In some examples, the particular angle of micro-oscillations may vary after each of the one or more of the steps α, but may be at least β. In some examples, the pattern 915 includes additional or fewer steps α, larger or smaller steps α, and/or a macro-oscillation of a greater or smaller angle than 180 degrees.

Figure 10:
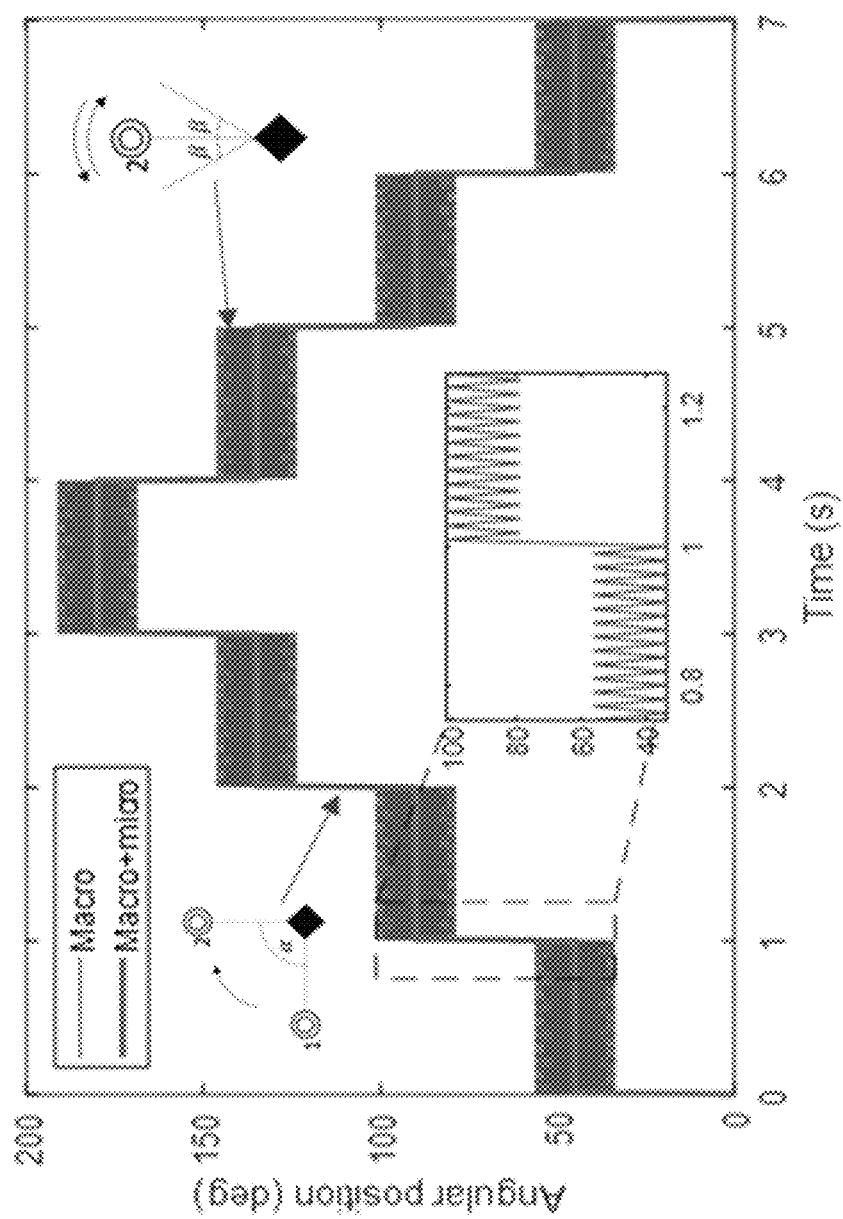
FIG. 10 illustrates an oscillation pattern in the form of a plot of rotation angle versus time.

Referring now to FIG. 10, an oscillation pattern 1000 is illustrated in the form of a plot of rotation angle (e.g., of the HFMs 34, central shaft 228, drive shaft 11, etc.) versus time. The oscillation pattern 1000 may be implemented by the electronic controller 12 (driving the motor 10) to oscillate the HFMs 34, for example, to implement block 815 of the process 800. The oscillation pattern 1000 is another oscillation pattern with superimposed oscillations including macro-oscillations and micro-oscillations occurring between steps α of the macro-oscillations. The oscillation pattern 1000 includes 180 degree macro-oscillations with 45 degree steps α separated every 1 second. After each step, the oscillation pattern 1000 includes 22.5 degree micro-oscillations (i.e., β equals 22.5 degrees). In this example, the rotation for the micro-oscillations and steps occur at an angular velocity of 3200 degrees/second. In some examples, characteristics of the oscillation pattern 1000 may be modified. For example, the pattern 1000 may include additional or fewer steps α, larger or smaller steps α, a macro-oscillation of a greater or smaller angle than 180 degrees, and/or may rotate with a different or varying angular velocity.

FIGS. 11A-11F and 11H-11K illustrate further examples of rotational oscillation patterns in the form of a plot of rotation angle (e.g., of the HFMs 34, central shaft 228, drive shaft 11, etc.) versus time, similar to the plot of FIG. 10. These further examples of oscillation patterns may also be implemented by the electronic controller 12 (driving the motor 10) to oscillate the HFMs 34, for example, to implement block 815 of the process 800. Additionally, similar to the pattern 1000 of FIG. 10, the motor 10 may be driven to cause the illustrated patterns of FIGS. 11A-11K to repeat multiple times (e.g., continuously) during operation of the oxygenation system 200 or 100 (e.g., in block 815 of the process 800).

Starting with FIG. 11A, an oscillation pattern 1100 is provided that has constant rotational velocity. In particular, FIG. 11A shows the oscillation pattern 1100 having a constant macro-oscillation velocity during steps α and a constant micro-oscillation velocity during micro-oscillations (having angle β). Turning to FIG. 11B, an oscillation pattern 1105 having a macro-oscillation velocity during steps α that is different than a micro-oscillation velocity during micro-oscillations (having angle β). In particular, the micro-oscillation velocity is higher (faster) than the macro-oscillation velocity in the oscillation pattern 1105. In other examples, the oscillation pattern 1105 includes a micro-oscillation velocity that is lower (slower) than the macro-oscillation velocity. In the oscillation pattern 1105, the macro-oscillation velocity is constant across steps α and the micro-oscillation velocity is constant for each set of micro-oscillations. In other examples of the oscillation pattern 1105, one or more of the steps α may have a different macro-oscillation velocity than other steps α and/or one or more set of micro-oscillations may have a different micro-oscillation velocity than other sets of micro-oscillations.

FIG. 11C shows an oscillation pattern 1110 having a constant macro-oscillation velocity and micro-oscillation velocity, similar to pattern 1100 of FIG. 11A. However, in contrast to the pattern 1100, the pattern 1110 has macro-oscillations with steps α that are larger than the angle β of the micro-oscillations. FIG. 11D shows an extended version of the oscillation pattern 1110 shown in FIG. 11C.

Figure 11E:
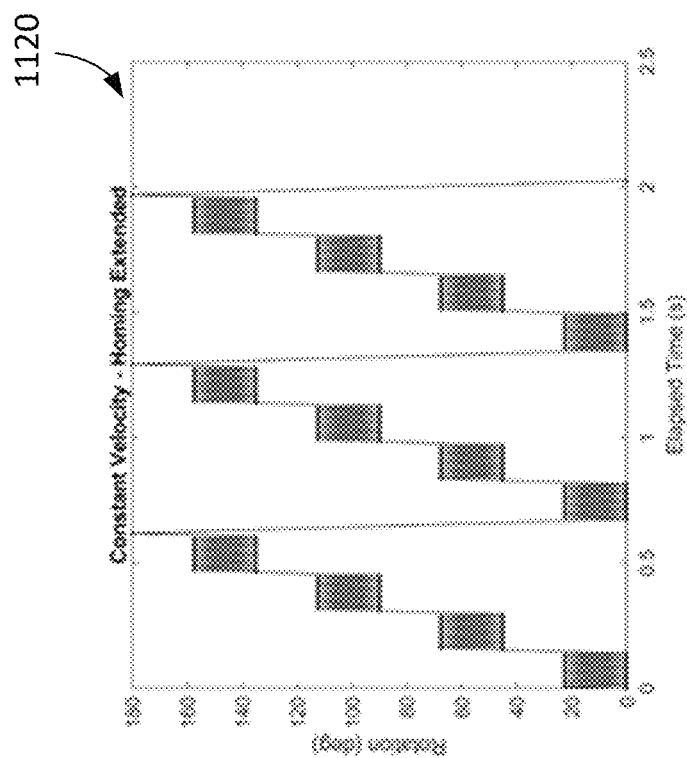
Figure 11F:
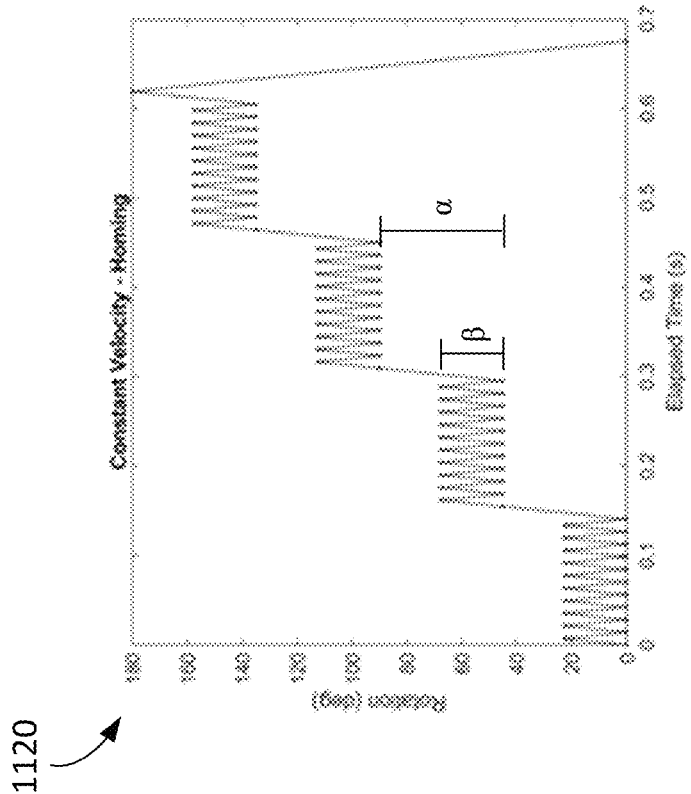

FIG. 11E shows an oscillation pattern 1120 having a constant macro-oscillation velocity and micro-oscillation velocity, similar to pattern 1100 of FIG. 11A. However, in contrast to the pattern 1100, the pattern 1120 is a homing pattern such that, after reaching the maximum rotational angle of the macro-oscillation (e.g., 180 degrees), the motor 10 rotates the HFMs 34 back to the starting position (e.g., 0 degrees) without intermediate steps α and micro-oscillations. In other words, the motor 10 superimposes micro-oscillations on the macro-oscillation of the HFMs 34 during one rotational direction of the macro-oscillation (e.g., clockwise), but not on the return rotational direction (e.g., counterclockwise) of the macro-oscillation. FIG. 11F shows an extended version of the homing oscillation pattern 1120 shown in FIG. 11F.

Figure 11H:
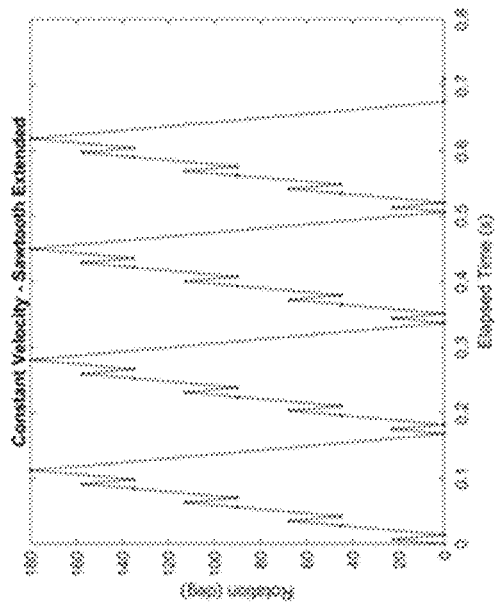
Figure 11I:
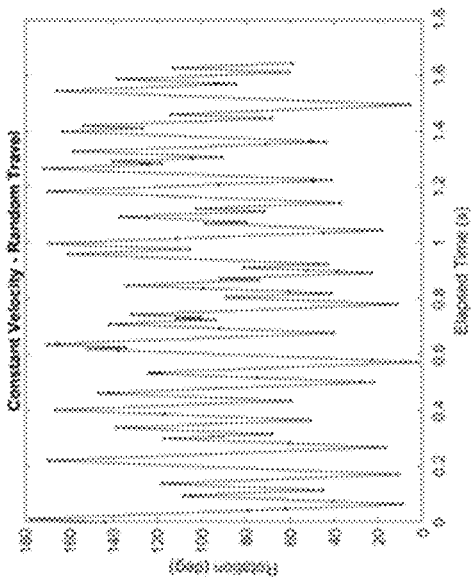

FIG. 11H shows a sawtooth oscillation pattern 1125 configured provide a sawtooth motion comprising a macro-oscillation including steps α with a single micro-oscillation after each step α on route from the starting angular position to the ending angular position of the macro-oscillation (i.e., from 0 degrees to 180 degrees). The sawtooth oscillation pattern 1125 in FIG. 11H also has a homing pattern in that the motor 10 rotates the HFMs 34 back to the starting angular position (e.g., 0 degrees) from the ending angular position (180 degrees) of the macro-oscillation without intermediate steps α and micro-oscillations. FIG. 11I shows an extended version of the sawtooth oscillation pattern 1125 shown in FIG. 11H.

Figure 11J:
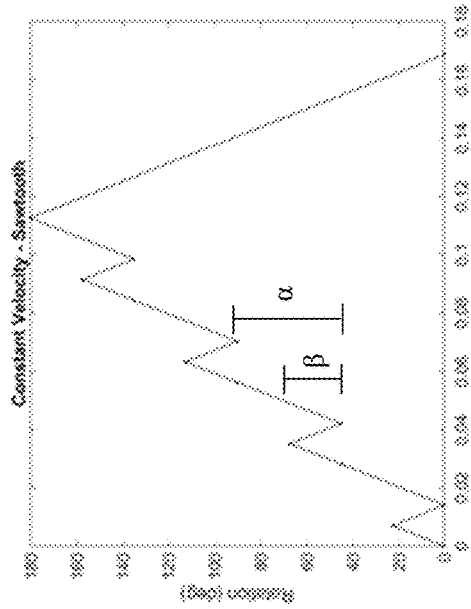

FIG. 11J shows an oscillation pattern 1130 having a constant macro-oscillation velocity and micro-oscillation velocity, similar to pattern 1100 of FIG. 11A. However, in contrast to the pattern 1100, the pattern 1130 having only two micro-oscillations after each step α.

Figure 11K:
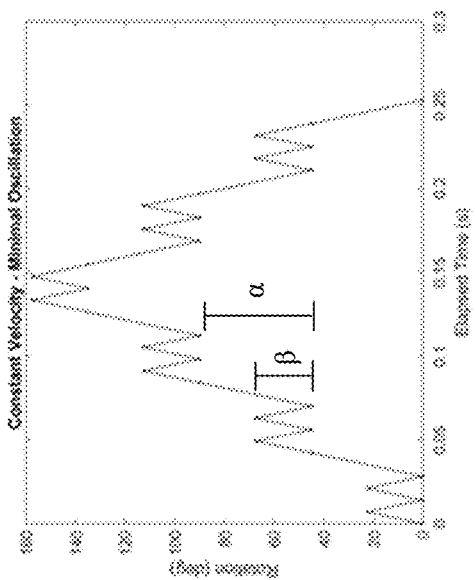

FIG. 11K shows an oscillation pattern 1135 that is configured to use random angles of oscillation. To implement the random oscillation pattern 1135, the electronic controller 12 may randomly select, at each vertex (or step) in the pattern, a rotational angle indicating a rotation amount and velocity indicating a rotational velocity to drive the motor 10 to the next vertex (with the rotation direction alternating between each vertex or step). The electronic controller 12 may select the rotational angle and velocity by executing various known random number generators or algorithms that are bounded with acceptable ranges for rotational angles and velocities for the oscillation pattern 1135.

The example oscillation patterns provided with respect to FIGS. 9A through 11K are non-limiting and can be used separately or in any combination by the systems described herein (including systems 100 and 200) to oscillate the HFMs 34. Additionally, the systems described herein may use other oscillation patterns not explicitly described herein to oscillate the HFMs 34.

Figure 12:
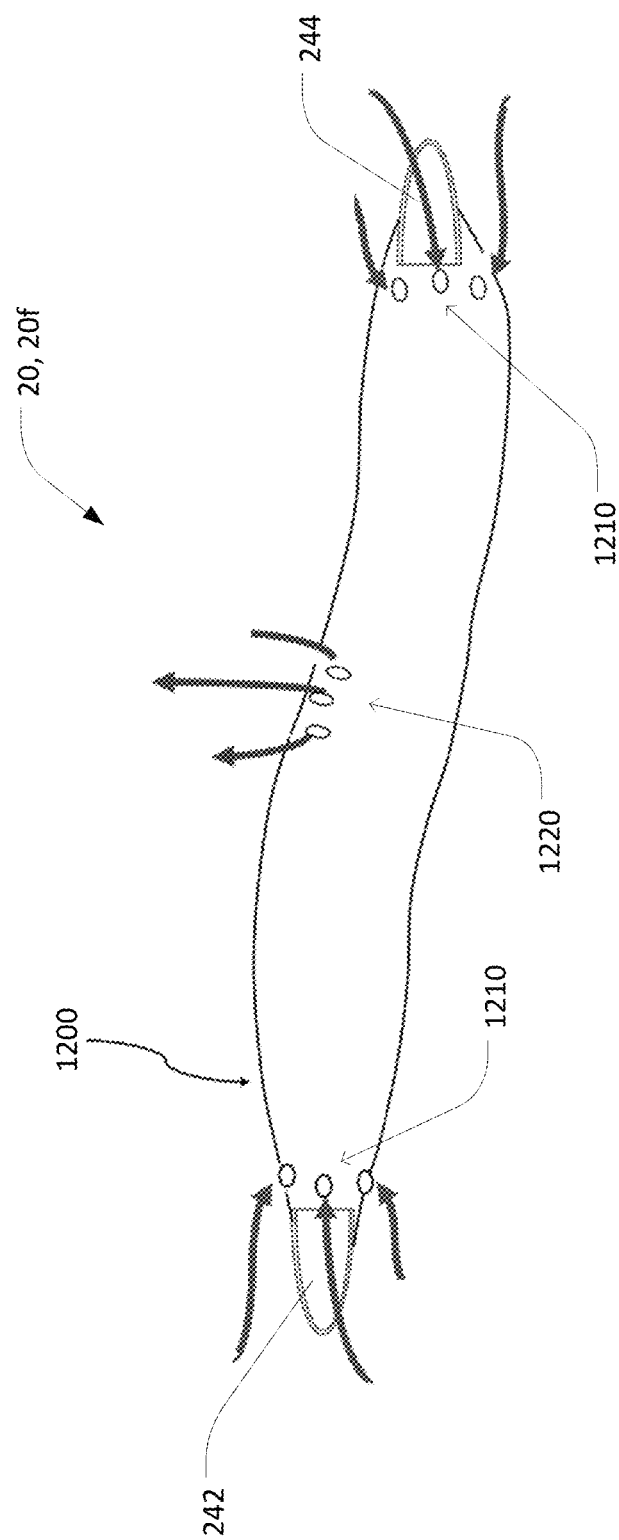
FIG. 12 illustrates another catheter according to some embodiments including a protective sheath.

Referring now to FIG. 12, a catheter 20f is illustrated. The catheter 20f is another embodiment of the catheter 20 referenced herein. The catheter 20f may be similar to the catheter 20c, except for any differences noted herein. In some embodiments, the oxygenation system 100 or 200 includes the catheter 20f as the catheter 20. Accordingly, the catheter 20f may be used by the systems 100 or 200 in implementing the process 800 of FIG. 8. In contrast to the catheter 20c, the catheter 20f includes a protective outer sheath 1200 as a protective guard in place of the protective guard 280. The HFMs 34 are entirely contained within the protective outer sheath 1200, and the protective outer sheath 1200 extends between a proximal end tip 242 and a distal end tip 244. The protective outer sheath 1200 may be coupled to the proximal end tip 242 and the distal end tip 244 similar to the manner in which the guard 280 is coupled to the end tips 242, 244, as described above, such that the protective sheath 1200 may be static (not rotating) while the HFMs 34 are oscillated.

The protective outer sheath 1200 may contain blood inlets 1210 at proximal and distal ends of the sheath that are configured to urge blood inward towards the HFMs. The protective outer sheath 1200 also may contain blood outlets 1220 located between the proximal and distal end of the sheath that are configured to expel oxygenated blood outward in an area of interest of a subject. In some aspects, the protective outer sheath 1200 does not have any openings on its surface other than the blood inlets 1210 and blood outlets 1220. During operation of the system 100 or 200 utilizing the catheter 20f, blood is urged inward to interact with the oscillating HFMs 34 within the protective outer sheath 1200 to be oxygenated, and then expelled outward via the blood outlets 1220 in the area of interest of the subject. In some examples, a micro-axial pump (see, e.g., pump 360 of FIG. 13) is provided within the protective sheath 1200 to provide urging forces to urge blood in through the blood inlets 1210 and to expel the oxygenated blood out through the blood outlets 1220. In some examples, the HFMs 34 are configurated such that the oscillation thereof provides urging forces to urge blood in through the blood inlets 1210 and to expel the oxygenated blood out through the blood outlets 1220 (see, e.g., discussion of HFMs with respect to FIGS. 14-17H below).

Figure 13:
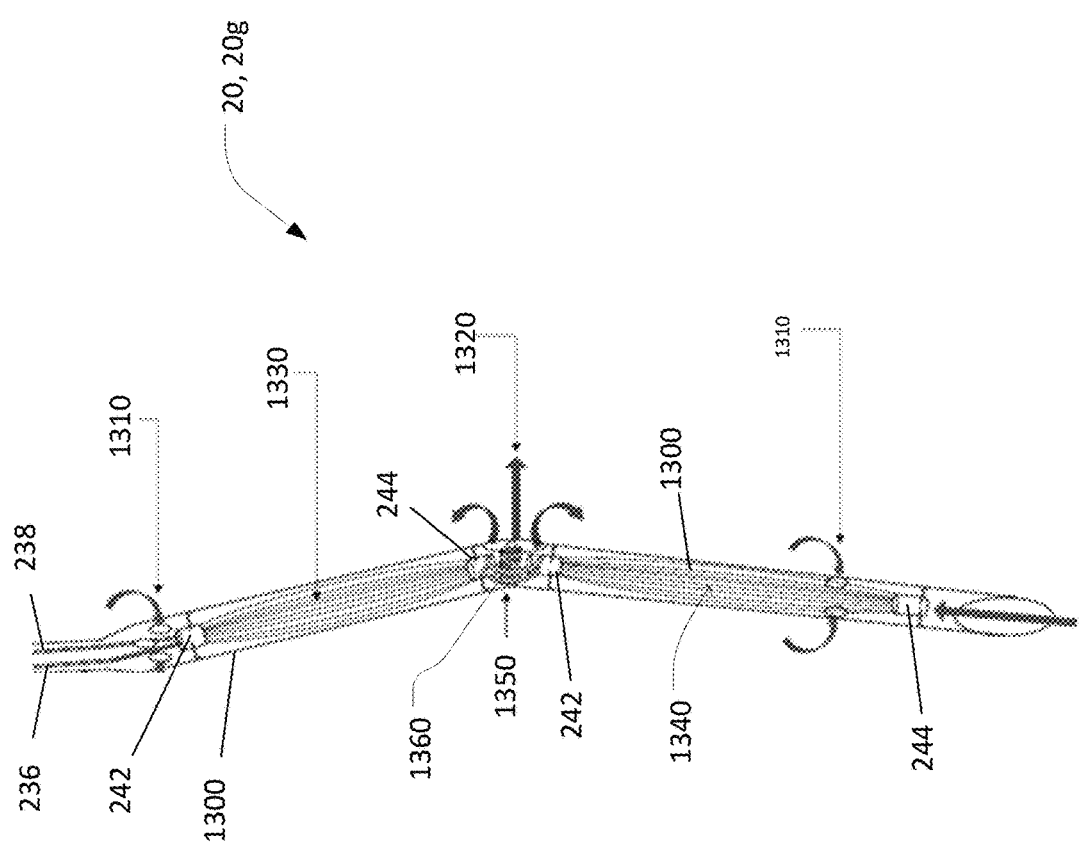
FIG. 13 illustrates another catheter according to some embodiments including a flexible joint and a micro-axial pump.

Referring now to FIG. 13, a catheter 20g is illustrated. The catheter 20g is another embodiment of the catheter 20 referenced herein. The catheter 20g may be similar to the catheter 20f, except for any differences noted herein. In some embodiments, the oxygenation system 100 or 200 includes the catheter 20g as the catheter 20. Accordingly, the catheter 20g may be used by the systems 100 or 200 in implementing the process 800 of FIG. 8. In contrast to the catheter 20f, the catheter 20g includes a flexible joint 1350 that can join at least a plurality of first HFMs 1330 with a plurality of second HFMs 1340. The HFMs 1330 and 1340 may each be an example of a bundle of HFMs 34, such as previously described. The flexible joint 1350 can contain a micro-axial pump 1360 that can pull blood in through blood inlets 1310 of a protective sheath 1300 and through the pluralities of HFMs 1330 and 1340. The flexible joint 1350 can be connected to a distal end of a plurality of first HFMs 1330 and connected to a proximal end of a plurality of second HFMs 1340, or the flexible joint 1350 can be connected to the pluralities of HFMs in various other combinations. Additionally, the micro-axial pump 360 can be configured to pump blood through the pluralities of HFMs and urge oxygenated blood outward through blood outlets 1320 of the protective sheath 1300 (e.g., towards a tricuspid valve of a subject). The protective sheath 1300 may be generally similar to the protective sheath 1200 of FIG. 12, except extended to cover each set of HFMs 1330 and 1340 and for different locations of the inlets 1310 and outlets 1320.

Figure 14:
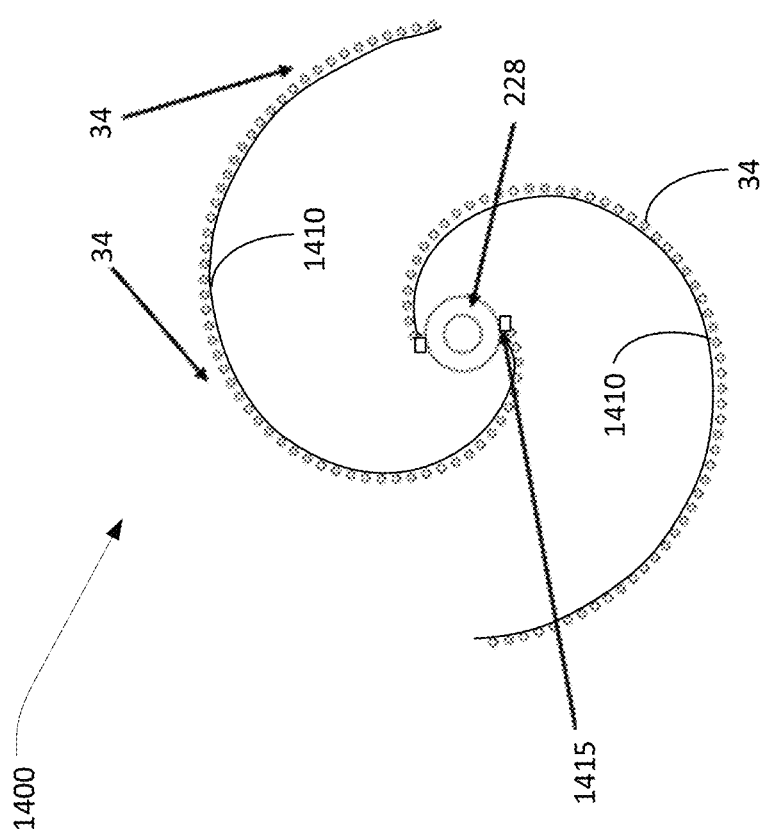
FIG. 14 is an illustration of a cross-sectional view of a spacing mechanism for HFMs.

Referring now to FIG. 14, a cross-sectional view of a spacing mechanism 1400 is shown. The spacing mechanism 1400 may be used in conjunction with the HFMs 34 in the various embodiments provided herein, including as part of the various catheters 20 and systems (e.g., systems 100 and 200) provided herein. The spacing mechanism 1400 can include at least one spiral support member 1410 that is connected to the central shaft 228 at an attachment point 1415 (e.g., via an adhesive). In the illustrated spacing mechanism 1400 includes two spiral support members 1410, although only one or more than two spiral support members 1410 are used in other examples. Each spiral support member 1410 is configured to retain a subset of the HFMs 34 in a spiral configuration relative to the central shaft 228, where the HFMs 34 generally extend parallel to one another. For example, the spiral support member(s) 1410 may include a weave (e.g., of interwoven fibers) through which the HFMs 34 pass and by which the HFMs 34 are retained. Additionally, in some examples, the spiral support member(s) 1410 retain their respective HFMs 34 in a non-woven configuration.

Figures 15A, 15B:
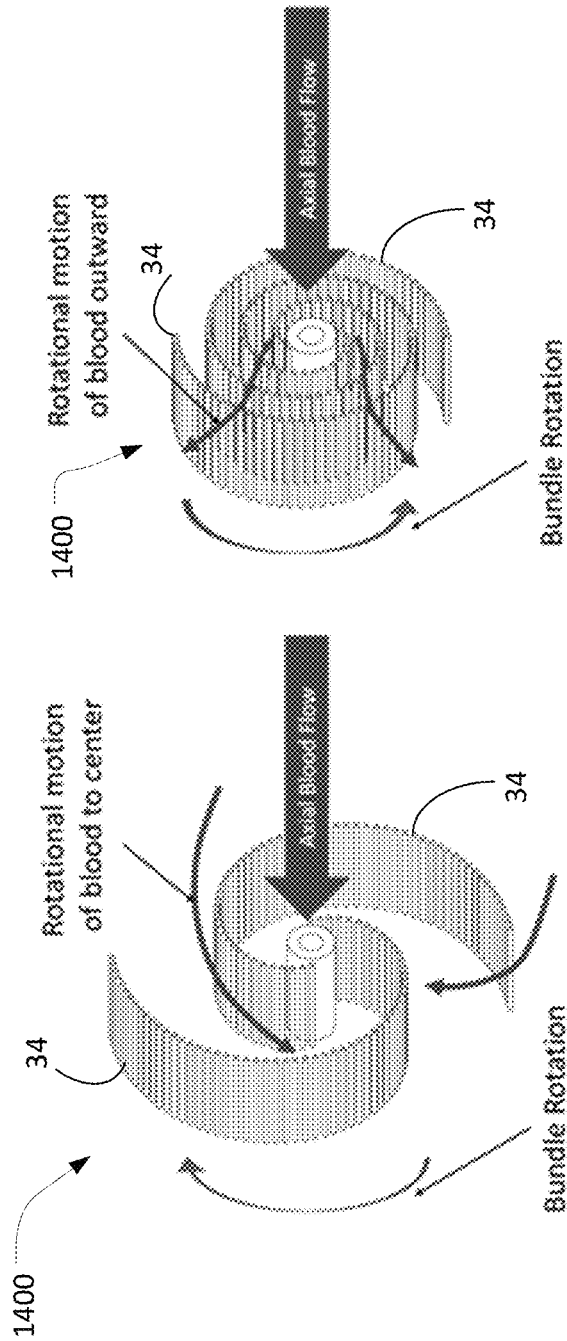
FIG. 15A is an example illustration of a scooping configuration of the spacing mechanism of FIG. 14.
FIG. 15B is an example illustration of a squeezing configuration of the spacing mechanism of FIG. 14.

FIGS. 15A-15B provide partial perspective views of the spacing mechanism 1400 used with the HFMs 34 in two different states, a scooping state (FIG. 15A) and a squeezing state (FIG. 15B). The spiral support members 1410 of the spacing mechanism 1400 are no illustrated in FIGS. 15A and 15B, but the spiral arrangement of the two subsets of HFMs 34 resulting from the two spiral support members 1410 is illustrated. During oscillation of the HFMs 34 (e.g., in block 815 of process 800), the at least one spiral support member 1410 can be driven by the motor 10 to rotate in a first direction such that the at least one spiral support member 1410 expands radially outward and arranges the subset(s) of HFMs 34 in a scooping state. This scooping state can cause blood to be drawn in an inward radial direction towards the central shaft 228 to expose the drawn-in blood to the HFMs 34 to enable diffusive flux of oxygen into the drawn-in blood. Additionally, the at least one spiral support member 1410 can be driven by the motor 10 to rotate in a second direction such that the at least one spiral support member 1410 contracts radially inward and arranges the subset(s) of HFMs 34 in a squeezing state. This squeezing state can cause blood to be urged in an outward radial direction away from the central shaft 228. The scooping can increase the blood that is exposed to the HFMs 34 and the squeezing can increase the oxygenated blood exhausted away from the HFMs 34 back into an area of interest of a subject. By oscillating the spacing mechanism 1400 (and, thereby, the HFMs 34) by the motor 10, the HFMs 34 alternate between a scooping and squeezing state, which increases the flow of blood in and out of proximity and interaction with the HFMs 34. Accordingly, the alternating scooping and squeezing states can increase the diffusive flux of the oxygenated gas from the HFMs 34 to the blood in a region of interest of a subject.

Figure 16:
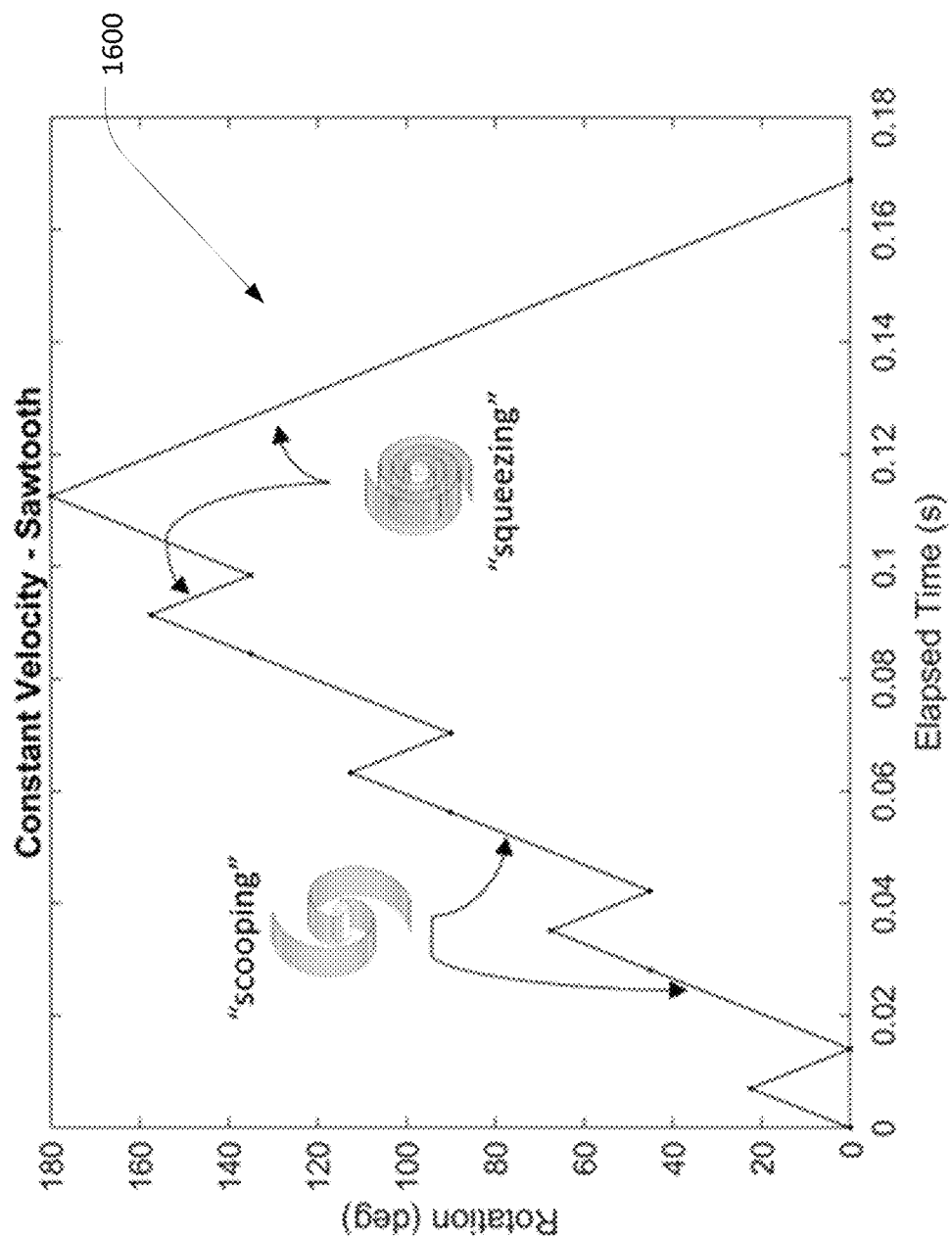
FIG. 16 is an example of a sawtooth rotational oscillation pattern that causes the HFMs to realize deployed scooping states and compressed squeezing states.

FIG. 16 shows an example sawtooth oscillation pattern 1600, similar to the sawtooth oscillation pattern 1125 of FIGS. 11H and 11I, that can be used to induce the scooping and squeezing states described above. In other examples, the motor 10 oscillates the spacing mechanisms 1400 (and HFMs 34) to induce the scooping and squeezing states using another oscillation pattern, such as one of the other oscillation patterns provided herein. In this example, the macro-oscillation steps α can induce expansion of the at least one spiral support member 1410 to result in the scooping state, and the micro-oscillations can induce retraction to result in the squeezing state. One skilled in the art will readily appreciate that this example is non-limiting and any number of oscillation patterns may be used to induce the rotational motion defined by the scooping and squeezing states. Additionally, in other aspects, the macro-oscillation steps may induce squeezing and the micro-oscillations may induce scooping, or another combination of macro- and micro-oscillations can be used to cause rotational motion of the at least one spiral support member 1410.

Figure 17A:
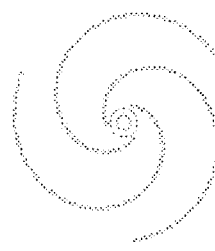
FIGS. 17A-17I illustrate various configurations of the spacing mechanism according to some embodiments.
Figure 17B:
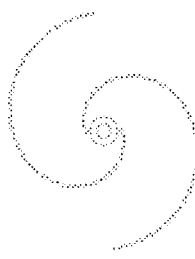
Figure 17C:
Figure 17D:
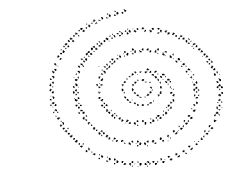
Figure 17E:
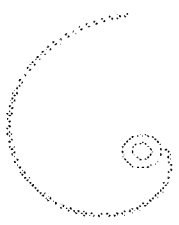
Figure 17F:
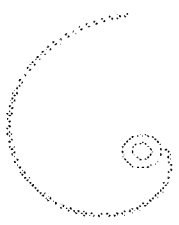
Figure 17G:
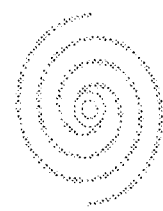
Figure 17H:
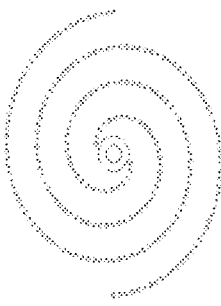
Figure 17I:
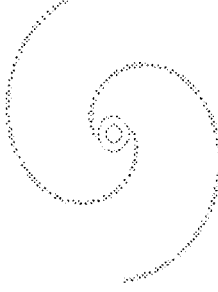

FIGS. 17A-H illustrate various arrangements of the at least one spiral support members 1410 of the spacing mechanism 1400 that may be used to arrange the HFMs 34. FIG. 17A shows an example spiral arrangement of a single spiral support member connected to the central shaft 228. FIG. 17B shows an example spiral arrangement of two spiral support members connected to the central shaft 228. FIG. 17C shows an example spiral arrangement of three spiral support members connected to the central shaft 228. FIG. 17D shows an example half wrap spiral arrangement of one spiral support member connected to the central shaft 228. FIG. 17E shows an example triple wrap spiral arrangement of one spiral support member connected to the central shaft 228. FIG. 17F shows an example compressed triple wrap spiral arrangement of one spiral support member connected to the central shaft 228. 17G shows an example half wrap spiral arrangement of two spiral support members connected to the central shaft 228. FIG. 17H shows an example triple wrap spiral arrangement of two spiral support members connected to the central shaft 228. FIG. 17I shows an example compressed triple wrap spiral arrangement of two spiral support members connected to the central shaft 228. One skilled in the art will readily appreciate that these examples are non-limiting and any number of spiral support members may be used to arrange the HFMs 34. In other aspects, arrangements other than spiral arrangements can be used to arrange the HFMs 34.

The disclosed systems and methods that include oscillating HFMs can improve oxygen mass transfer in a subject by both disrupting liquid boundary layer formation external to the hollow fibers and by increasing the exposure of fibers to differing areas of bulk fluid in the system. The oscillations, including those oscillation patterns with superimposed angular oscillations, combined with the hyperbaric membrane approach can result in oxygen transfer efficiencies greater than any previously reported in the literature.

In an example embodiment, the systems provided herein (also referred to as IntraVascular Membrane Oxygenators (IVMOs)), are intended to deliver oxygen, the primary deficit in most forms of acute lung injury. The disclosed systems and methods can require less total HFM surface area and allow for a more compact device amenable to intravascular use, overcoming challenges faced by previous groups.

Figure 18:
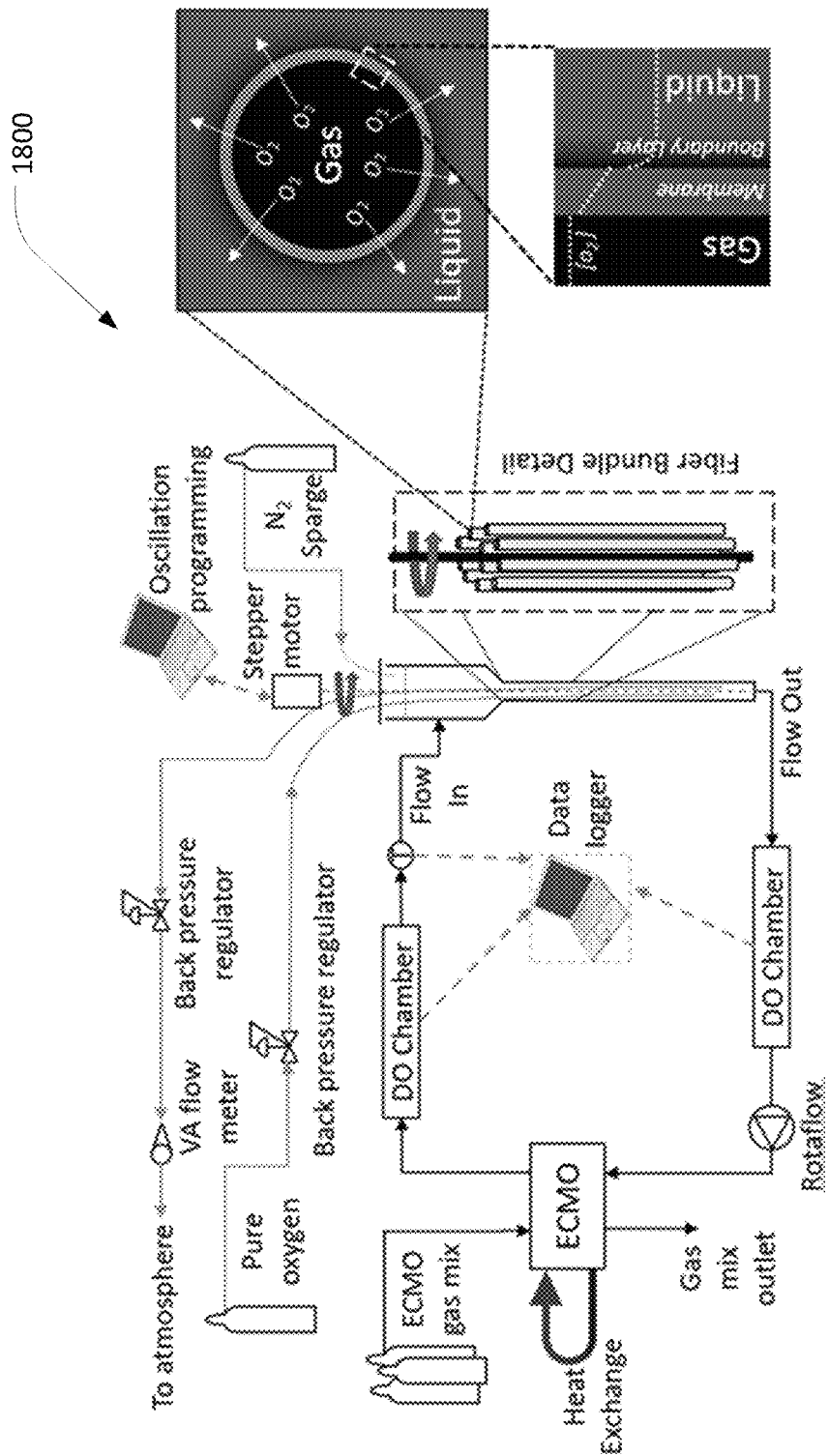
FIG. 18 is a schematic diagram of an experimental circuit used for HFM experimentation using water.

Referring now to FIG. 18, a schematic diagram of an experimental circuit 1800 used for HFM experimentation is shown. Specifically, the experimental circuit 1800 was built to test the impact of oscillation on oxygen flux from hollow fiber membranes (HFMs) that have high-pressure oxygen flowing through their lumens. The HFMs are located in the reactor and are attached to a stepper motor via a rotary shaft. High pressure oxygen flows through the HFM loops as water as a test fluid for experimentation (or blood in clinical cases) flows past at varying speeds. The increase in dissolved oxygen in the water (or blood) is measured. An ECMO membrane with nitrogen flowing through in series is used to de-oxygenate the water to the desired baseline for experimental purposes.

Figure 19:
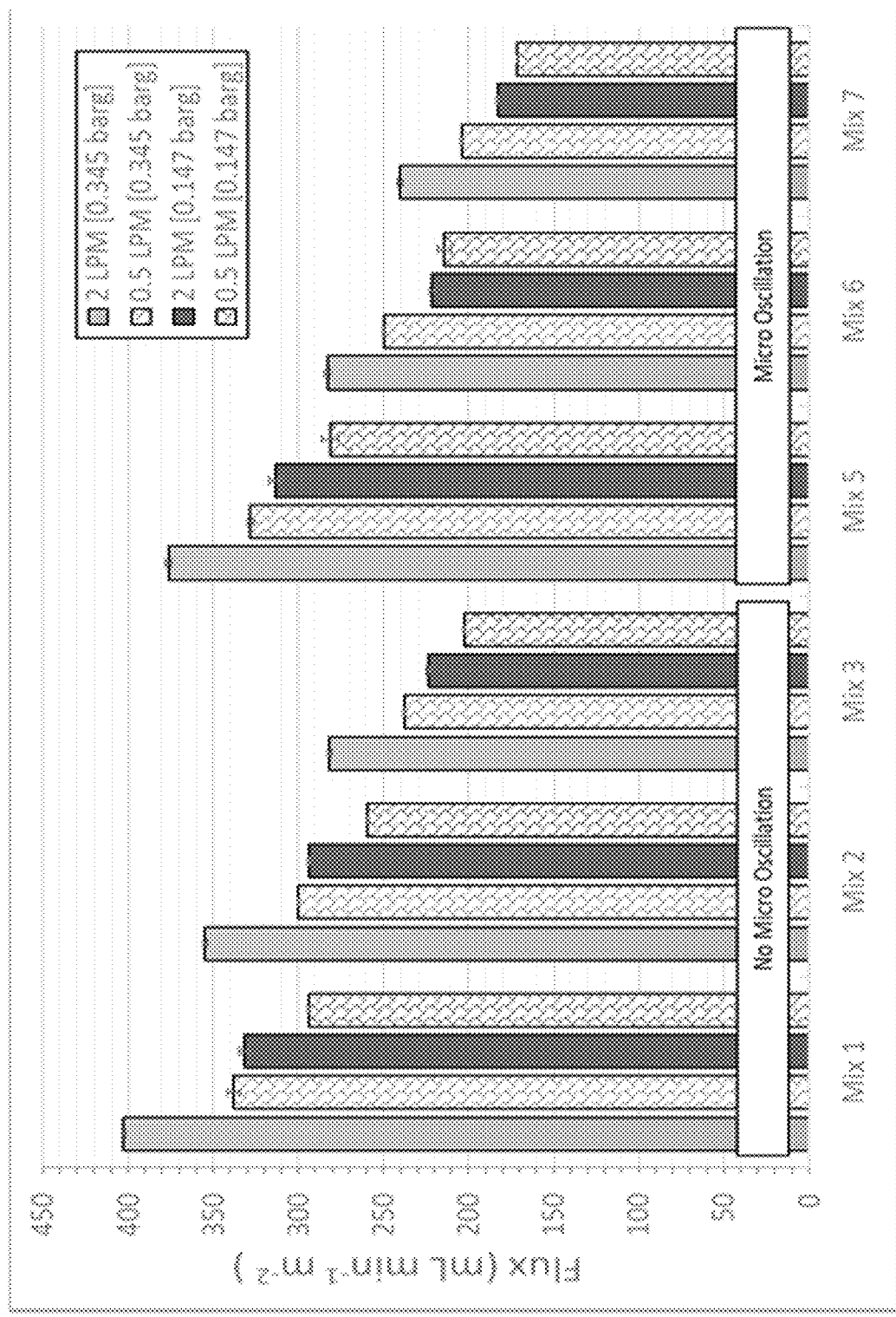
FIG. 19 is a chart of experimentally determined oxygen flux at selected angular speeds of oscillation and pressure.

FIG. 19 shows the results of the experimentally determined oxygen flux at selected angular speeds of oscillation. The panel on the left represents a 32 fiber bundle oscillating back and forth 180 degrees (at various speeds as indicated by mixes 1, 2, 3). The panel on right represents the fiber bundle oscillating with macro-oscillations of 180 degrees in 22.5 degree increments (steps α=22.5 degrees) with 11.5 degree micro-oscillations (β=11.5 degrees) superimposed, and executed at various speeds as indicated by mixes 5, 6, 7. Specifically, the mixing regimes were at high (1.345 bar absolute pressure (0.345 barg)) and low (1.147 bar absolute pressure (0.147 barg)) pressures under two flow conditions (0.5 and 2.0 LPM) with mixing regimes 1 through 3, and 5 through 7 being 3200, 1600, 720 degrees/second, respectively, using the described oscillation. Experiments were performed in water at 37 degree C., with a viscosity of 3.5 cP, and flowing through the mock vena cava reactor at both 0.5 and 2 liters/minute to mimic physiologic conditions. The resulting data shows that oxygen flux increases with increased angular speed of the oscillations, and that rotational oscillation provides much improved oxygen flux compared to static fibers. Further, only a slight decrease in oxygen flux was observed for the mixes 5, 6, and 7, relative to mixes 1, 2, and 3, resulting from the superimposed micro-oscillations. Additionally, oscillations of HFMs, and even more so oscillations with superimposed micro-oscillations, provide reduced bubble generation, as discussed further with respect to FIG. 20, and the slight decrease in flux from superimposed micro-oscillations can be mitigated by increasing the oscillation speed.

Figure 20:
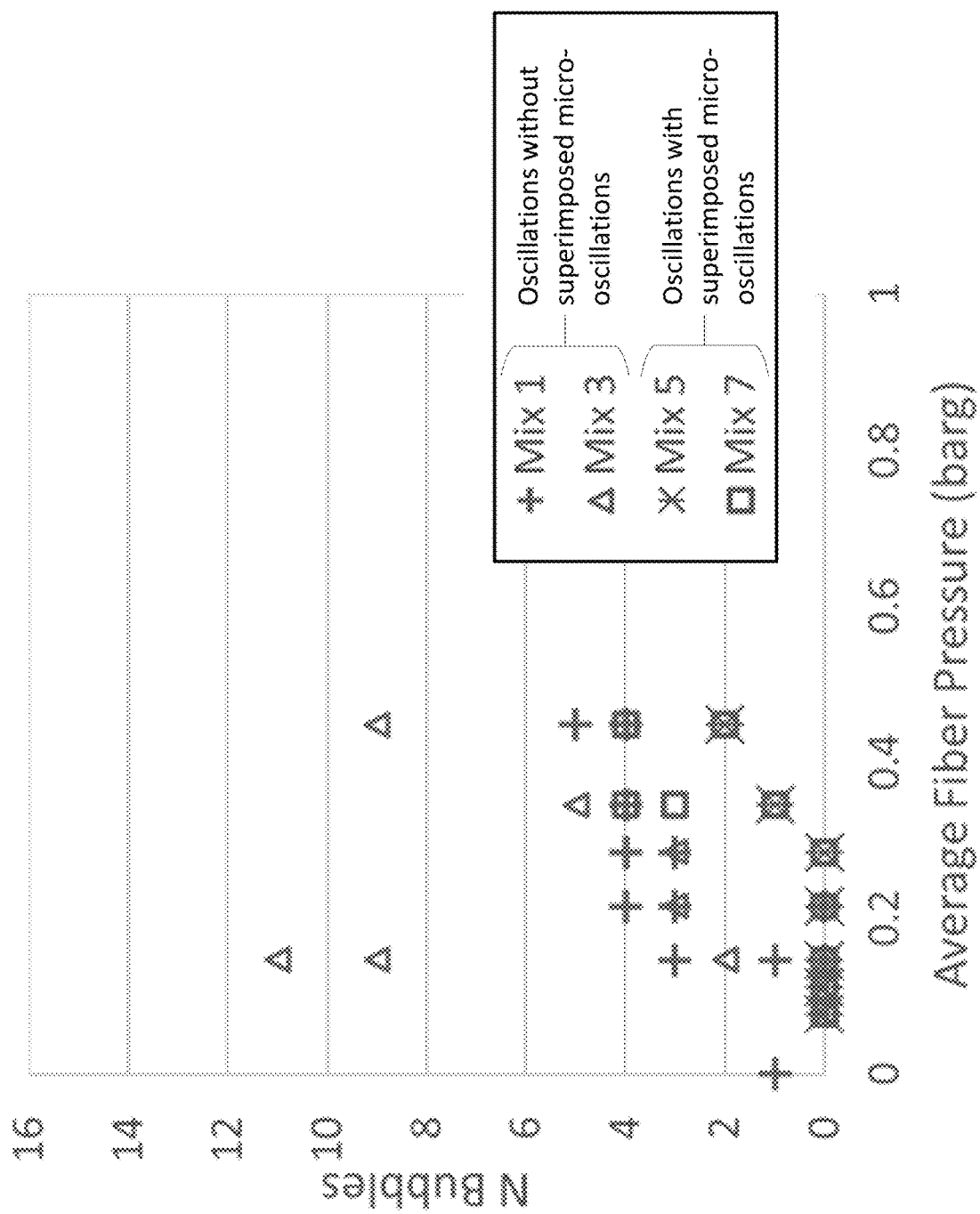
FIG. 20 is a chart of an experimentally determined number of bubbles for a single loop of fiber in an aqueous solution.

FIG. 20 shows the results of the experimentally determined number of bubbles for a single loop of fiber C (34 cm total length in correlation with the average gage fiber pressure). Experiments were performed at 0.5 LPM system flow rate under 4 mixing regimes. Mixes 1 and 3 were rotationally oscillated 180 degrees, without micro-oscillation, at 3200 and 720 degrees/second respectively. Mixes 5 and 7 were rotationally oscillated at 3200 and 720 degrees/second, respectively, with macro-oscillations of 180 degrees in 22.5 degree increments (i.e., steps α=22.5 degrees) with 11.5 degree micro-oscillations (β=11.5 degrees) superimposed at each step. Decreased bubble formation was found to occur when micro-oscillations were superimposed upon macro-oscillations (mixes 5 and 7). Accordingly, by superimposing micro-oscillations upon macro-oscillations, bubble formation is decreased and/or eliminated. The reduction in bubbles, in turn, enables operation of the oxygenation system (e.g., system 100 or 200) at higher intraluminal pressure (i.e., the oxygenated gas can be at a higher pressure), which results in increased diffusive flux of oxygen. At least in some examples, without this superimposed micro-oscillation technique, bubble formation may increase to an undesirable level at these higher intraluminal pressures, thereby preventing a system from increasing the pressure of the oxygenated gas to achieve a desired diffusive flux of oxygen. Stated another way, generally, as pressure of the oxygenated gas in the HFMs 34 increases, diffusive flux of oxygen increases and bubble formation increases. However, oscillating the HFMs 34, particularly rotationally oscillating the HFMs 34 with micro-oscillations superimposed on macro-oscillations, reduces the bubble formation, thereby enabling an increase in the pressure of the oxygenated gas and in the resulting diffusive flux of oxygen into blood without the corresponding increase in bubbles.

Figure 21:
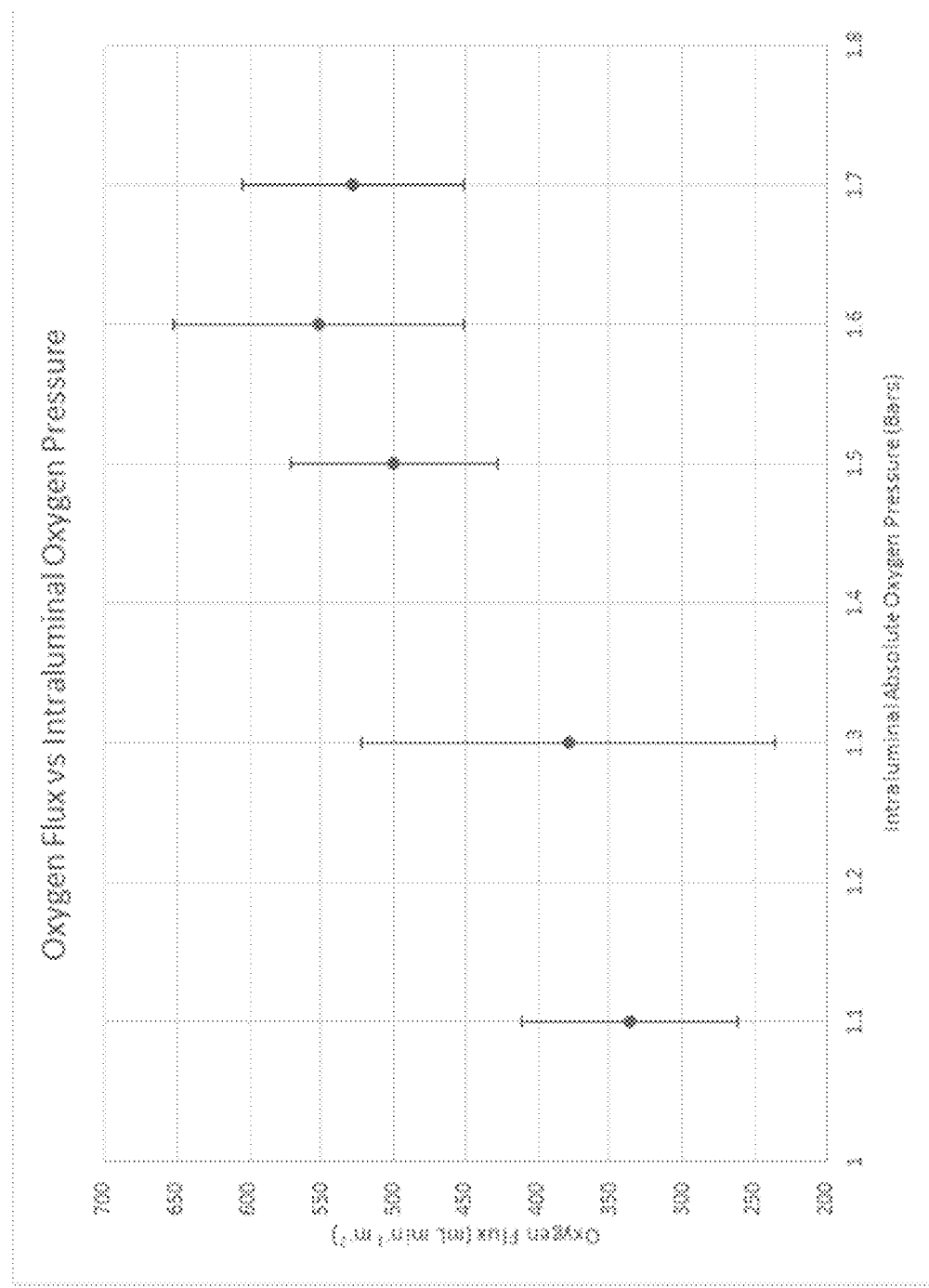
FIG. 21 is a chart of experimentally determined oxygen flux of a hollow fiber member (HFM) bundle prototype undergoing superimposed angular oscillation.

FIG. 21 shows experimentally determined oxygen flux of a hollow fiber bundle prototype (total diffusing surface area of 0.22 m$^2$) undergoing superimposed angular oscillations (macro-oscillations with step α at 22.5 degrees, micro-oscillations with angle β at 45 degrees, angular velocity 3200 degrees/second). Experiments were performed in vitro using porcine whole blood flowing at 3 L min−1 in accordance with ISO 7199. Increased oxygen flux was found to occur at higher intraluminal absolute oxygen pressures.

Figure 22:
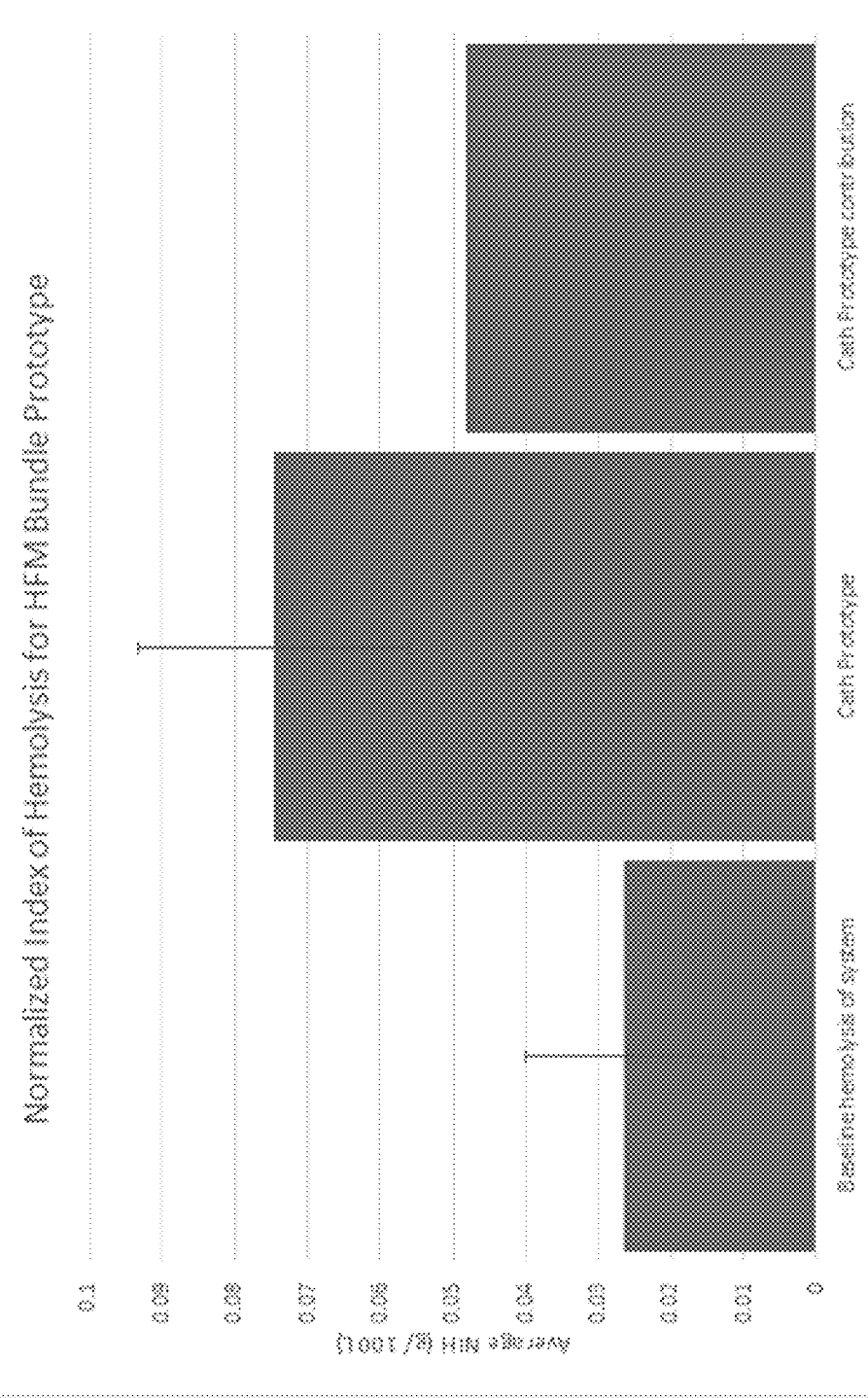
FIG. 22 is a chart of experimentally determined normalized index of hemolysis of a hollow fiber bundle prototype undergoing superimposed angular oscillations.

FIG. 22 shows an experimentally determined normalized index of hemolysis of a hollow fiber bundle prototype (total diffusing surface area of 0.22 m$^2$) undergoing superimposed angular oscillations (macro-oscillations with step α at 22.5 degrees, micro-oscillations with angle β at 45 degrees, angular velocity 3200 degrees/second). Experiments were performed in vitro using porcine whole blood flowing at 3 liters/minute in accordance with the American Society for Testing and Materials (ASTM) standard F1841-19. The rate of hemolysis attributed to catheter prototype using this experimental setup was found to be within a clinically acceptable range (<0.05 g/100 L).

In a series of experiments, the hyperbaric approach to membrane oxygenation with HFMs in combination with oscillating the HFMs was tested. Active mixing was accomplished using superimposed angular oscillation of the HFM bundle, as described herein. The HFM bundle was secured to a central shaft that was rotated at various speeds over 180 degrees of total rotation arc. A stepper motor and controller were used to set the motor's rotational speed (degrees/second), total arc traveled, and oscillation settings. The bundles of fiber were created to fit within a 1.5 cm diameter using a mesh spacer at two locations. Travel of an individual fiber is illustrated for macro steps over angle α followed by micro-oscillations over angle β. When this system was tested under physiologic conditions (2 L/min flow of aqueous PEG solution to match viscosity of whole blood at 3.5 cP and 37° C.) it delivered approximately 300 mL O$_2$/(min*m$^2$) at only 5 PSI (or 1.345 bar) intraluminal oxygen pressure. This result was an approximately 100% increase in flux when compared to the static fibers in earlier testing. When a thinner wall fiber (OD 305 μm with 38 μm wall thickness) was used at the same low intraluminal pressures (5 PSI, 1.345 bar) the oxygen flux increased to 400 mL O2 min−1 m−2, surpassing even that of the present previous high pressure (27.5 PSI, 2.9 bar) static tests.

Figure 23:
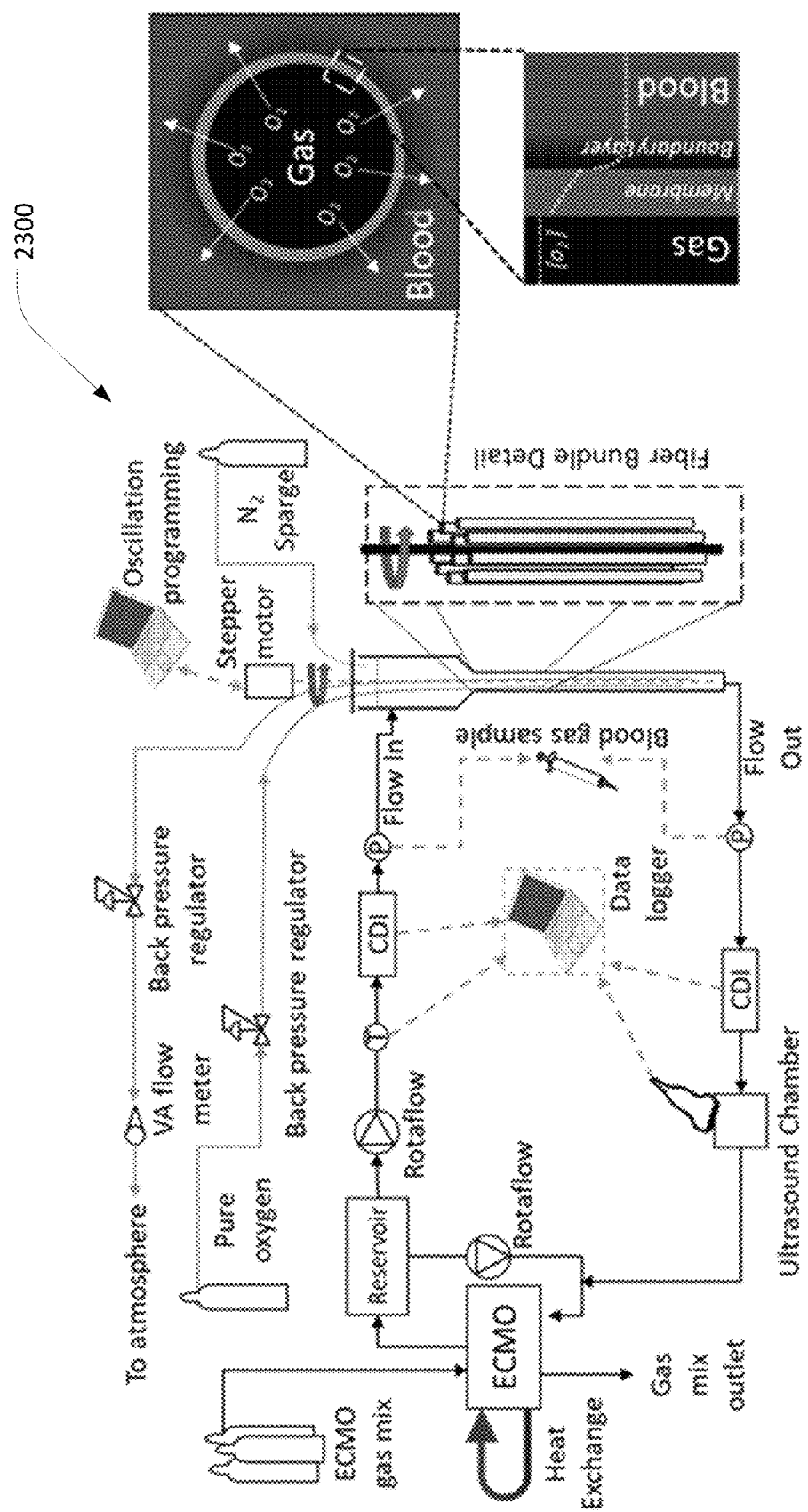
FIG. 23 is a process schematic of a benchtop experimental setup for testing in porcine blood.

FIG. 23 is a process schematic of a benchtop experimental setup for testing in porcine blood. This setup included an ex vivo benchtop circuit 2300 capable of mimicking intravascular conditions in accordance with ISO 7199. The HFM bundles were placed in the 2 cm ID reactor and oscillated by a stepper motor and controller so that it was possible to set the motor's rotational speed (degrees/second), total arc traveled, and oscillation settings, similar to the present previous work. Porcine whole blood collected via venipuncture from donor animals was obtained and used within 48 hours of collection. Blood was pumped past the hollow fiber bundle reactor at 3 L/min and inlet blood conditions were held constant in accordance with ISO 7199 (temperature 37° C., % oxyhemoglobin saturation 65±5, base excess 0±5 mmol/L, PaCO2 45±5 mmHg) using a membrane oxygenator (Maquet/Getinge AB, Goteborg, Sweden) with a custom blend sweep gas. Inlet and outlet blood gas samples were taken and analyzed using a GEM Premiere 3000 blood gas analyzer (Werfen, Bedford, MA) and Avoximeter 4000 (Werfen, Bedford, MA). A Teflon AF 2400 hollow fiber bundle composed of 68 fibers (32.8 cm in length) using fibers (OD of 254 μm and 38.1 μm wall thickness) was tested. The HFM bundle was made to fit within a 2 cm diameter using a mesh spacer at three locations. When placed in porcine whole blood with hemoglobin values between 9 and 11 g/dL value of, and with an average intraluminal oxygen pressure of 1.1 to 1.7 bar absolute, oxygen flux averages ranging from 336 to 552 mL O$_2$/(min*m$^2$), were observed. A maximum of 708 mL O$_2$/(min*m$^2$) was observed at 1.6 bar absolute oxygen pressure.

These series of experiments demonstrate the high oxygen transfer efficiency (oxygen flux) of the present novel approach to membrane oxygenation. By combining a high-pressure oxygen gradient across non-porous HFMs undergoing oscillation (e.g., according to one of the oscillation patterns provided herein), the systems and methods are able to reduce the impacts of both internal and external barriers to oxygen mass transfer and can achieve oxygen fluxes higher than those reported in the literature. When tested in blood under the conditions described above, the system demonstrates on average over a 150% increase in oxygen flux compared to the IVOX device that was tested in human clinical trials (552 mL O$_2$/(min*m$^2$) vs 219 mL O$_2$/(min*m$^2$) and a 23% increase upon the highest oxygen flux previously reported in the literature for any intravascular gas exchange device (552 mL O$_2$/(min*m$^2$) vs 450 mL O$_2$/(min*m$^2$) reported by the group developing the HIMOX device.

Flux efficiency achieved in previous work by Hattler et al. with extreme mixing (10,000 RPM) and more modest balloon pulsing methods (300 BPM) resulted in maximum flux of around 374 mL O$_2$/(min*m$^2$) and 140 mL O$_2$/(min*m$^2$), respectively. In experiments using approaches provided herein, with oscillation of HFMs at oxygenated gas at 1.1 bar absolute pressure or more, the oxygen flux exceeded previous work by Hattler et al. and the present inventors using static HFM diffusive flux, resulting in flux efficiencies of 500 mL $O_2$/(min*$m^2$) and above. For example, in testing with a system similar to the system 200 with the catheter 20c, with average intraluminal oxygen pressure of 1.1 to 1.7 bar absolute, oxygen flux averages ranged from 336 to 552 mL $O_2$/(min*$m^2$), and a maximum of 708 mL $O_2$/(min*$m^2$) was observed at 1.6 bar absolute oxygen pressure. In these tests, the HFMs 34 were oscillated with an oscillation pattern having macro-oscillations including steps α with angle of 22.5 degrees and micro-oscillations with β angle of 45 degrees (at 3200 degrees per second). These results show a significant improvement in oxygen flux (approximately 150% of the flux of Hattler et al.) when the system operates at 1.6 bar and with greatly reduced rotation speeds. More particularly, the example rotation speeds to produce the oscillations in the tests were only approximately 533 RPM in whole blood, compared to 10,000 RPM. Accordingly, the results illustrate a significant improvement in flux with significantly less mixing, which improves biocompatibility of the system with a subject.

Accordingly, oxygenation systems and methods provided herein use hyperbaric intraluminal oxygen pressure, which enables high diffusion through HFMs, combined with oscillations of the HFMs that increase the efficiency of the diffusion through the HFMs relative to static HFMs. In some examples, micro-oscillations are superimposed on the oscillations (i.e., on oscillations of larger angles, also referred to as macro-oscillations), which can ensure that oxygen in the HFMs that is diffused through the HFMs is dissolved into solution (into a subject's blood) with decreased or no bubble formation. Because these oscillation techniques decrease or eliminate bubbles, the HFMs can operate at hyperbaric pressure and at higher levels than previously employable. Further, because higher pressure levels can be used, an increase in oxygen flux and transfer efficiency results. Further, the increased oxygen flux and transfer efficiency (using hyperbaric pressure and oscillation) enables reduction in gas diffusing surface area of the HFMs. In other words, the size of the HFM bundle may be more compact and, thus more amenable to intravascular use.

It is to be understood that the ranges described herein are non-limiting example ranges. Input parameters such as the rotation speed, angle of rotation, and time between oscillations can be varied in order to optimize the bubble reduction and increase oxygen flux for a particular subject.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. The present disclosure shall control in the event there are any disparities between any definitions and/or description found in any incorporated references.

The invention claimed is:

1. An intravascular gas exchange system, the system comprising:
   a pneumatic inlet configured to couple to a pneumatic source that provides a gas at a pressure at or above 1.1 bar of absolute pressure;
   a plurality of hollow fiber membranes (HFM) in pneumatic communication with the pneumatic inlet to receive the gas and with an outlet for exhaust gas,
      wherein a diffusive flux of the gas flows from the plurality of HFMs in a region of interest of a subject, and
      wherein an average intraluminal pressure in the plurality of HFMs is at or above 1.1 bar of absolute pressure;
   a vacuum system pneumatically coupled to the plurality of HFMs; and
   an electronic controller coupled to the vacuum system and configured to control the vacuum system to de-pressurize the plurality of HFMs in response to detecting that a pressure change value in the plurality of HFMs has exceeded a threshold.

2. The intravascular gas exchange system of claim 1, wherein, in response to detecting that the pressure change value in the plurality of HFMs has exceeded the threshold, the electronic controller is further configured to:
   control an inlet valve to cease flow of the gas to the pneumatic inlet, and
   control a controllable valve to connect a vacuum source of the vacuum system to the plurality of HFMs.

3. The intravascular gas exchange system of claim 1, wherein, in response to detecting that the pressure change value in the plurality of HFMs has exceeded the threshold, the electronic controller is further configured to:
   control a controllable valve to connect a pump of the vacuum system to the plurality of HFMs.

4. The intravascular gas exchange system of claim 1, wherein the electronic controller is further configured to cause oscillation of the plurality of HFMs.

5. The intravascular gas exchange system of claim 4, further comprising:
   a motor coupled to the plurality of HFMs,
   wherein, to cause oscillation of the plurality of HFMs, the electronic controller is coupled to the motor and configured to drive the motor.

6. The intravascular gas exchange system of claim 4, wherein, to cause oscillation of the plurality of HFMs, the electronic controller is configured to cause superimposed angular oscillations to the plurality of HFMs including macro-oscillations, comprised of steps α, superimposed with micro-oscillations with at least an oscillation angle of β.

7. The intravascular gas exchange system of claim 6, wherein α is in a range of approximately 1-360 degrees, and β is in a range of approximately 1-180 degrees, and wherein the gas is at a pressure at or between 1.1 bar and 5.0 bar of absolute pressure.

8. The intravascular gas exchange system of claim 6, wherein, to provide the superimposed angular oscillations to the plurality of HFMs, at each step α of the macro-oscillations, the electronic controller is configured to drive a motor to oscillate with the micro-oscillations with at least the oscillation angle of β to define an oscillation pattern.

9. The intravascular gas exchange system of claim 6, wherein the superimposed angular oscillations reduce bubble formation in the region of interest of the subject.

10. The intravascular gas exchange system of claim 4, wherein, to cause oscillation of the plurality of HFMs, the electronic controller is configured to drive a motor to oscillate with random angles of oscillations.

11. The intravascular gas exchange system of claim 4, wherein the intravascular gas exchange system is configured to achieve a diffusive flux of the gas at or above 500 mL per minute per square meter.

12. The intravascular gas exchange system of claim 1, wherein the gas is oxygenated gas and the exhaust gas is deoxygenated gas.

13. The intravascular gas exchange system of claim 12, wherein the diffusive flux of the oxygenated gas is at or between 336 mL per minute per square meter and 708 mL per minute per square meter.

14. A method for intravascular gas exchange, the method comprising:
receiving, by a pneumatic inlet coupled to a pneumatic source, a gas at a pressure at or above 1.1 bar of absolute pressure;
receiving the gas, by a plurality of hollow fiber membranes (HFM) in pneumatic communication with the pneumatic inlet, wherein an average intraluminal pressure in the plurality of HFMs is at or above 1.1 bar of absolute pressure;
detecting, by an electronic controller, that a pressure change value in the plurality of HFMs has exceeded a threshold; and
controlling, by the electronic controller, a vacuum system to de-pressurize the plurality of HFMs in response to detecting that the pressure change value in the plurality of HFMs has exceeded the threshold.

15. The method of claim 14, further comprising:
in response to the electronic controller detecting that the pressure change value in the plurality of HFMs has exceeded the threshold:
controlling an inlet valve to cease flow of the gas to the pneumatic inlet, and
controlling an outlet valve to cease flow of exhaust gas out of the plurality of HFMs.

16. The method of claim 14, further comprising:
in response to the electronic controller detecting that the pressure change value in the plurality of HFMs has exceeded the threshold, controlling a controllable valve to connect a pump of the vacuum system to the plurality of HFMs.

17. The method of claim 14, further comprising:
oscillating the plurality of HFMs to cause a diffusive flux of the gas from an interior of the plurality of HFMs in a region of interest of a subject,
wherein the diffusive flux of the gas is at least 336 milliliters per minute per square meter.

18. The method of claim 17, further comprising:
wherein oscillating the plurality of HFMs comprises driving a motor, by the electronic controller, to provide superimposed angular oscillations to the plurality of HFMs including macro-oscillations, comprised of steps α, superimposed with micro-oscillations with at least an oscillation angle of β.

19. The method of claim 14, the method further comprising:
compressing, by one or more of a retractable sheath or a rotational winding of the plurality of HFMs around a central shaft, the plurality of HFMs to define a travelling state conformation; and
deploying the plurality of HFMs to a deployed state conformation by one or more of retracting the retractable sheath or rotationally unwinding the plurality of HFMs.

20. The method of claim 14, the method further comprising:
receiving, from the pneumatic inlet, the gas by a central shaft extending between a proximal end tip and a distal end tip;
retaining, by the proximal end tip, proximal ends of the plurality of HFMs; and
retaining, by the distal end tip, distal ends of the plurality of HFMs.

* * * * *